United States Patent
Ludwig

(10) Patent No.: US 8,660,823 B2
(45) Date of Patent: Feb. 25, 2014

(54) NONLINEAR AND LIE ALGEBRA STRUCTURAL ANALYSIS SYSTEM FOR ENZYME CASCADES, METABOLIC SIGNAL TRANSDUCTION, SIGNALING PATHWAYS, CATALYTIC CHEMICAL REACTION NETWORKS, AND IMMUNOLOGY

(75) Inventor: Lester F. Ludwig, Belmont, CA (US)

(73) Assignee: Lester F. Ludwig, San Antonio, TX (US)

( * ) Notice: Subject to any disclaimer, the term of this patent is extended or adjusted under 35 U.S.C. 154(b) by 181 days.

(21) Appl. No.: 12/767,794

(22) Filed: Apr. 26, 2010

(65) Prior Publication Data
US 2010/0274540 A1 Oct. 28, 2010

Related U.S. Application Data

(60) Provisional application No. 61/214,643, filed on Apr. 26, 2009.

(51) Int. Cl.
G06F 17/50 (2006.01)
G06F 7/60 (2006.01)
G06G 7/48 (2006.01)

(52) U.S. Cl.
USPC ............. 703/2; 703/1; 703/6; 703/11; 703/12

(58) Field of Classification Search
USPC ............................................. 703/1, 2, 6, 11
See application file for complete search history.

(56) References Cited

U.S. PATENT DOCUMENTS

| | | | |
|---|---|---|---|
| 6,859,735 B1* | 2/2005 | Stoughton et al. | 702/19 |
| 6,859,767 B2* | 2/2005 | Gratzl et al. | 702/194 |
| 7,353,152 B2* | 4/2008 | Brazhnik et al. | 703/11 |
| 7,472,050 B2* | 12/2008 | Defranoux et al. | 703/11 |
| 7,654,955 B2* | 2/2010 | Polidori et al. | 600/300 |
| 7,734,420 B2* | 6/2010 | Palsson et al. | 702/19 |
| 7,761,238 B2* | 7/2010 | Moser et al. | 702/19 |
| 7,787,754 B2* | 8/2010 | Patera et al. | 386/212 |
| 7,831,090 B1* | 11/2010 | Krishnan et al. | 382/154 |
| 7,853,406 B2* | 12/2010 | Michelson et al. | 702/19 |
| 7,856,317 B2* | 12/2010 | Schilling | 702/19 |
| 7,869,957 B2* | 1/2011 | Palsson et al. | 702/19 |

(Continued)

OTHER PUBLICATIONS

Hunter, P.J. "The IUPS Physiome Project: A Framework for Computational Physiology", Progress in Biophysics & Molecular Biology 85 (2004) 551-569.*

(Continued)

*Primary Examiner* — Shambhavi Patel
(74) *Attorney, Agent, or Firm* — Procopio, Cory Hargreaves & Savitch LLP

(57) ABSTRACT

A computer modeling system for study of behavior of complex signaling pathways is described. The computer modeling system includes a computer representation of one or more nonlinear models of at least one signaling pathway arrangement involving enzyme cascades and/or allosteric enzymes and feedback. The computer representation of the model is transformed into at least portions of a bilinear dynamical system representation from which a series of Lie bracket operations are computed and the result tested for transitivity conditions of the associated semisimple Lie matrix algebra so as to determine potential instabilities and crosstalk susceptibilities. Also, the computer model can additionally comprise accurate numerical simulations, equilibrium condition analysis tools, and other algebraic structural tools involving graphs and matroids. The computer representation further includes a modular model environment for models to evolve with new discovery, trial of experimental models, combining multiple nonlinear models into more complex models, interactive user environments, crosstalk study, and detailed comparative analysis.

20 Claims, 25 Drawing Sheets

(56) References Cited

U.S. PATENT DOCUMENTS

| | | | |
|---|---|---|---|
| 7,920,993 B2* | 4/2011 | Palsson et al. | 703/2 |
| 7,920,994 B2* | 4/2011 | Palsson et al. | 703/2 |
| 8,065,089 B1* | 11/2011 | Najarian | 702/19 |
| 8,285,523 B2* | 10/2012 | Mandal et al. | 703/2 |
| 2002/0019975 A1* | 2/2002 | Johnson | 717/117 |
| 2002/0091666 A1* | 7/2002 | Rice et al. | 707/1 |
| 2005/0074745 A1* | 4/2005 | Clayton et al. | 435/4 |
| 2005/0086035 A1* | 4/2005 | Peccoud et al. | 703/2 |
| 2007/0016390 A1* | 1/2007 | Bernardo et al. | 703/11 |
| 2011/0264432 A1* | 10/2011 | Penner et al. | 703/11 |

OTHER PUBLICATIONS

Hunter, P.J. "The IUPS Physiome Project: A Framework for Computational Physiology", Progress in Biophysics & Molecular . Biology 85 (2004) 551-569.*

Elliot, David. "Bilinear Systems", 2005.*

Babu et al. "Modeling and Simulation in Signal Transduction Pathways: A Systems Biology Approach", Biochimie 88 (2006) 277-283.*

Kuzmic, Petr. "A Generalized Numerical Approach to Rapid-Equilibrium Enzyme Kinetics: Application to 17β-HSD", Molecular and Cellular Endocrinology 248 (2006) 172-181.*

Oliveira et al. "An Algebraic-combinatorial Model for the Identification and Mapping of Biochemical Pathways", Bulletin of Mathematical Biology (2001) 63, 1163-1196.*

Koh et al. "A decompositional approach to parameter estimation in pathway modeling: a case study of the Akt and MAPK pathways and their crosstalk", Bioinformatics vol. 22 No. 14 2006, pp. e271-e280.*

Najdi ("Application of Generalized MWC Model for the Mathematical Simulation of Metabolic Pathways Regulated by Allosteric Enzymes".*

Markevich et al. "Signaling Switches and Bistability Arising from Multistate Phosphorylation in Protein Kinase Cascades", The Journal of Cell Biology, vol. 164, No. 3, Feb. 2, 2004 353-359.*

Agrachev et al. "Lie-algebraic conditions for exponential stability of switched systems", 1999.*

Breitling et al. "A structured approach for the engineering of biochemical network models, illustrated for signalling pathways", 2008.*

Bai et al. "A projection method for model reduction of bilinear dynamical systems", Linear Algebra and its Applications 415 (2006) 406-425.*

Chaves et al. "Exact computation of amplification for a class of nonlinear systems arising from cellular signaling pathways", 2006.*

Condon et al. "Krylov subspaces from bilinear representations of nonlinear systems", 2007.*

Geffen, Dara. "Parameter Identifiability of Biochemical Reaction Networks in Systems Biology", 2008.*

Heinrich et al. "Mathematical Models of Protein Kinase Signal Transduction", Molecular Cell, vol. 9, 957-970, May, 2002.*

Juang, Jer-Nan. "Generalized Bilinear System Identification", The Journal of the Astronautical Sciences, vol. 57, Nos. 1 & 2, Jan.-Jun. 2009, pp. 261-273.*

Krishnan et al. "Systems Analysis of Regulatory Processes Underlying Eukaryotic Gradient Perception", Special Issue on Systems Biology, Jan. 2008.*

Liebermeister et al. "Bringing metabolic networks to life: integration of kinetic, metabolic, and proteomic data", Theoretical Biology and Medical Modelling 2006, 3:42.*

Margaliot et al. Lie-algebraic stability conditions for nonlinear switched systems and differential inclusions, 2005.*

Noack et al. "Visualizing regulatory interdependencies and parameter sensitivities in biochemical network models", Mathematics and Computers in Simulation 79 (2008) 991-998.*

Pardoles, et al. "Bilinear Systems and Nonlinear Estimation Theory", 2008.*

Pardalos et al. "Nonlinear Dynamical Systems and Adaptive Filters in Biomedicine", Annals of Operations Research 119, 119-142, 2003.*

Soebiyanto et al. "From Networks to Systems to Complex Systems: A Signaling Pathway Coordination Case Study", 2005.*

Sontag, et al. "Structure and Stability of Certain Chemical Networks and Applications to the Kinetic Proofreading Model of T-Cell Receptor Signal Transduction", IEEE Transactions on Automatic Control, vol. 46, No. 7, Jul. 2001.*

Stelling et al. "Mathematical Modeling of Complex Regulatory Networks", IEEE Transactions on Nanobioscience, vol. 3, No. 3, Sep. 2004.*

Wang et al. "Stability Analysis of Biological Systems with Real Solution Classification", 2005.*

Zumsande et al. "Bifurcations and Chaos in the MAPK Signaling Cascade", 2010.*

\* cited by examiner

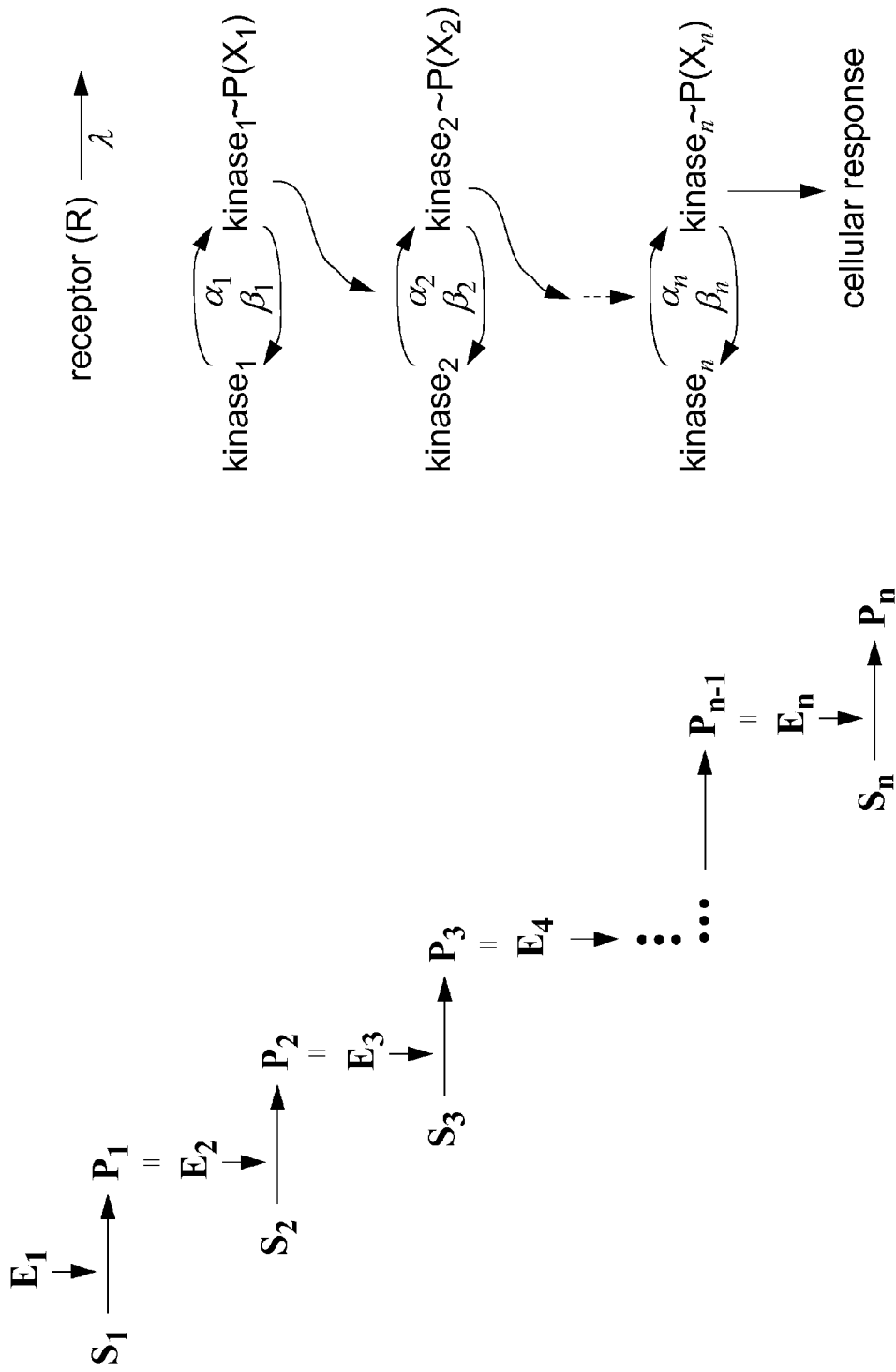

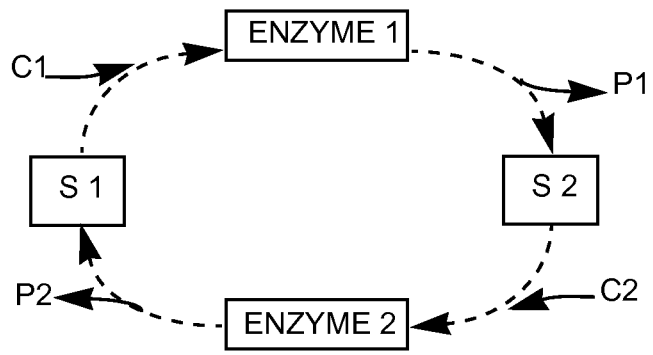
Figure 2a  *(Adapted from [PfScMS95])*
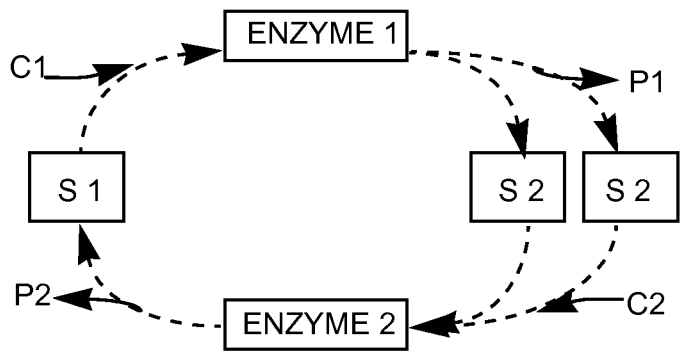
Figure 2b  *(Adapted from [PfScMS95])*

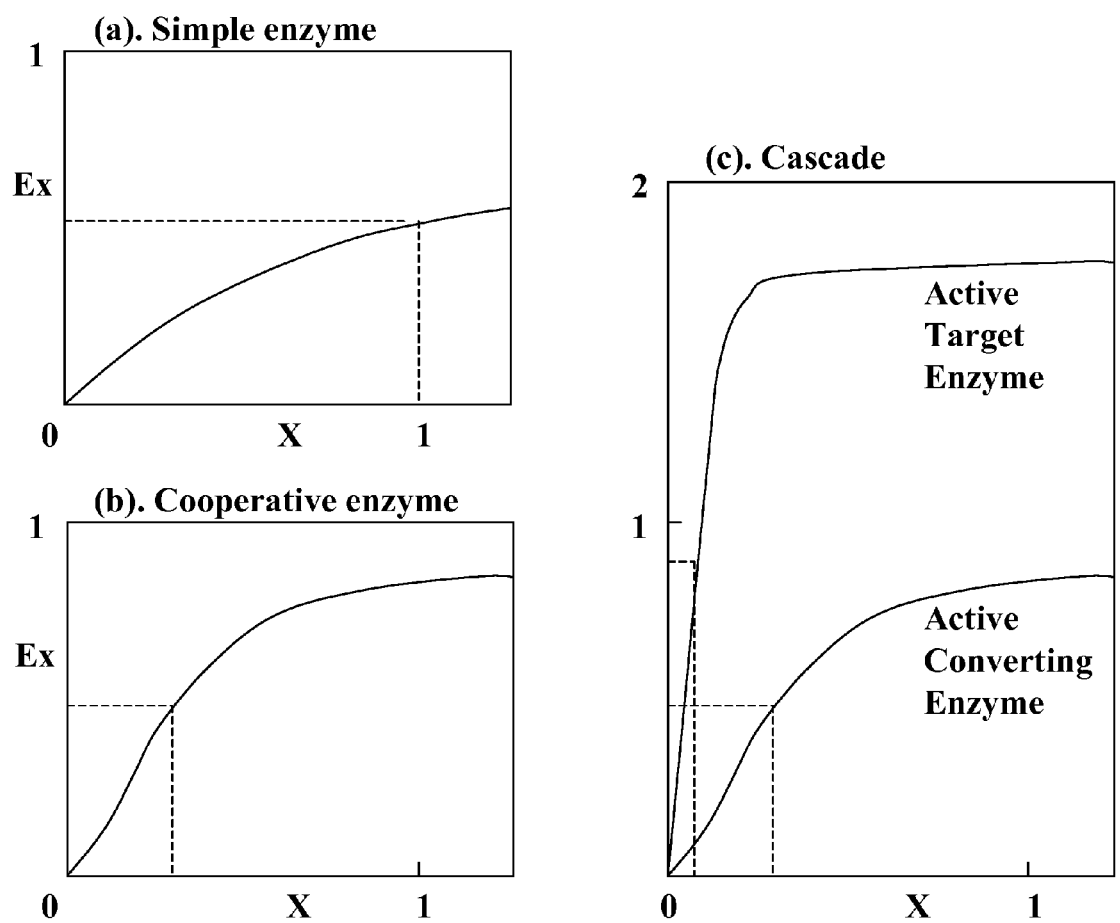
Figure 3a *(Adapted from [Roach 1977])*

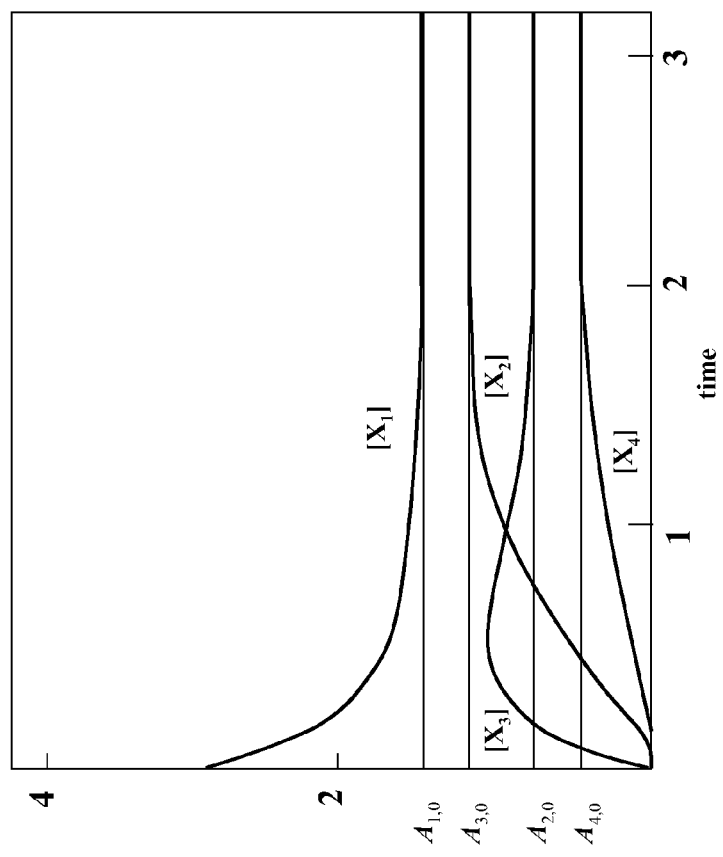
Figure 3c *(Adapted from [VarHav90])*
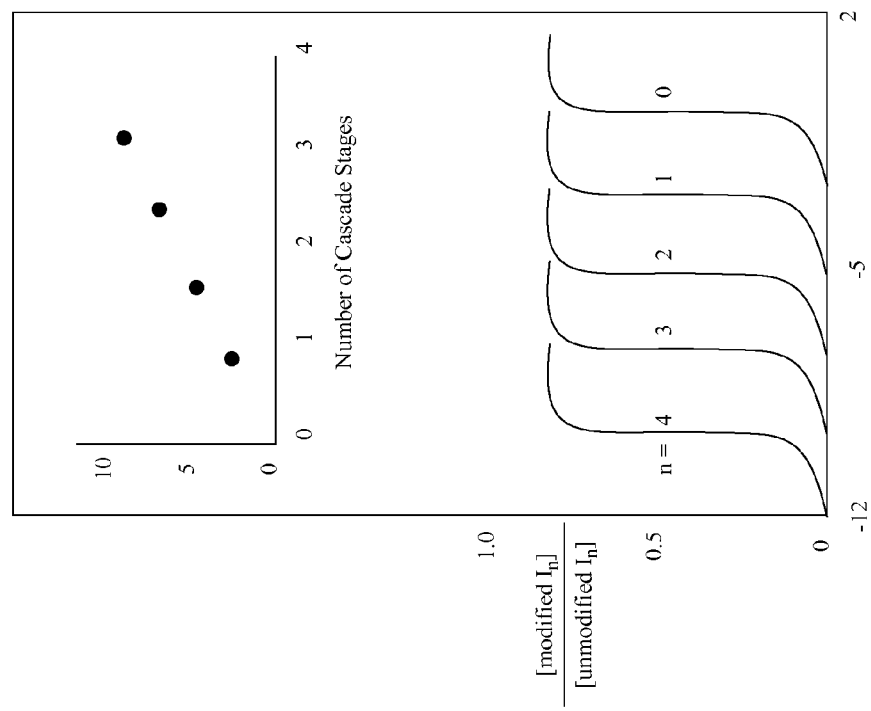
Figure 3b *(Adapted from [StaCho78])*

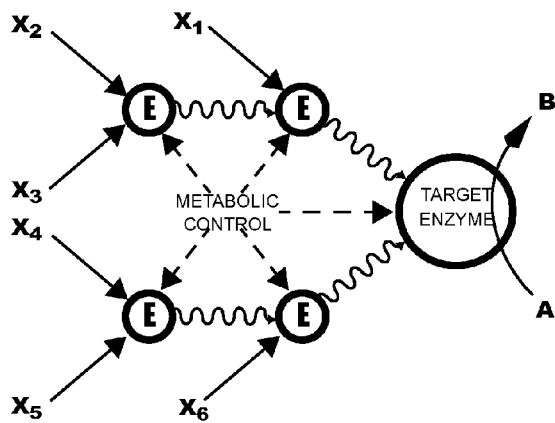
Figure 4a *(Adapted from [Roach 1977])*
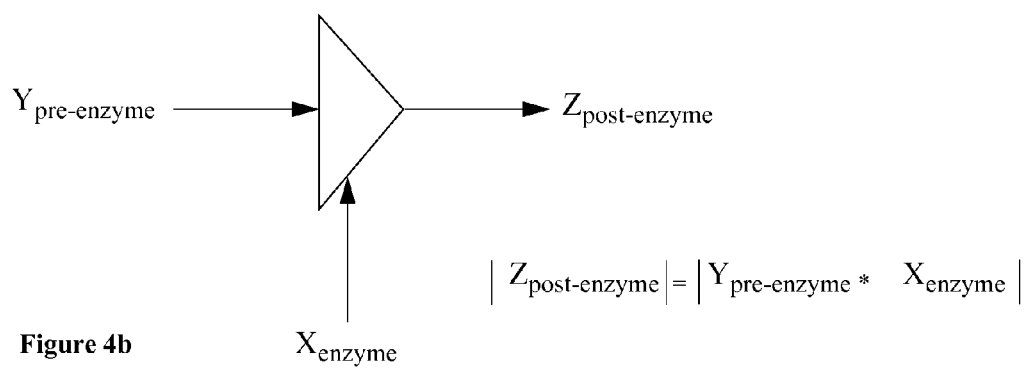
Figure 4b
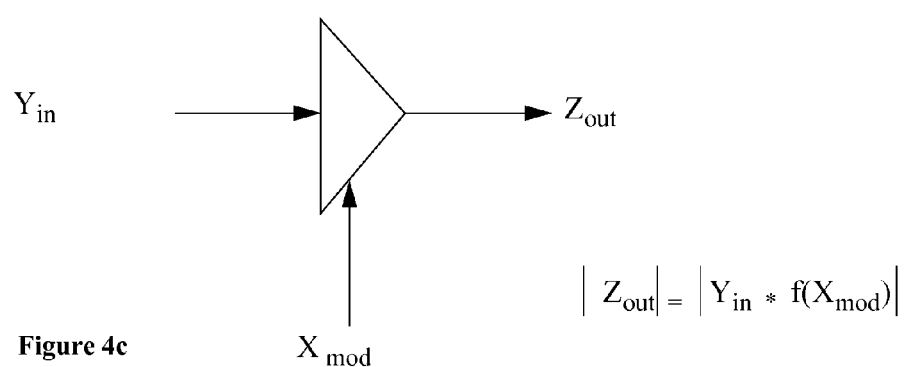
Figure 4c

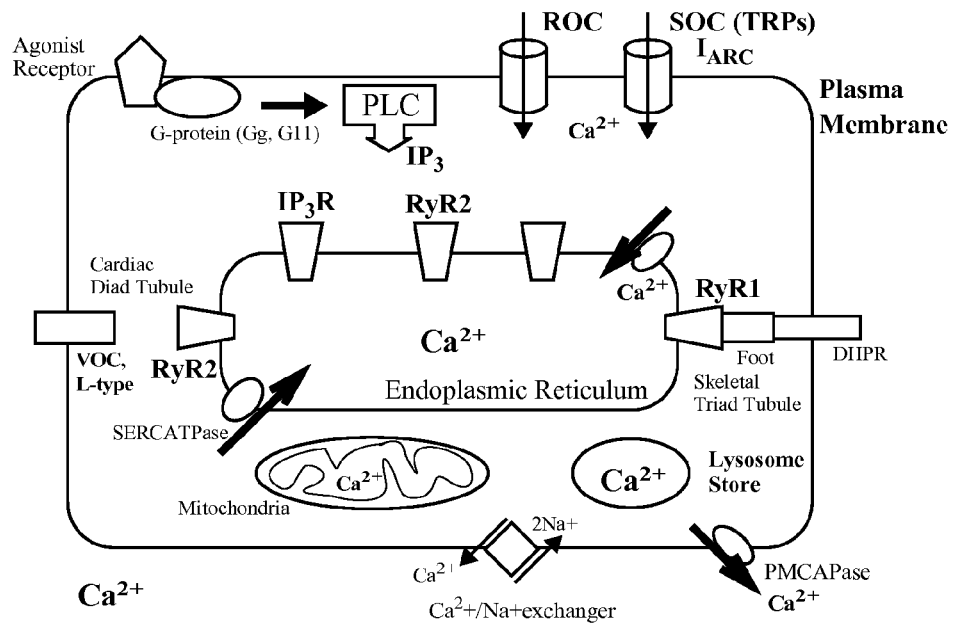
Figure 5a *(adapted from [Sander05])*
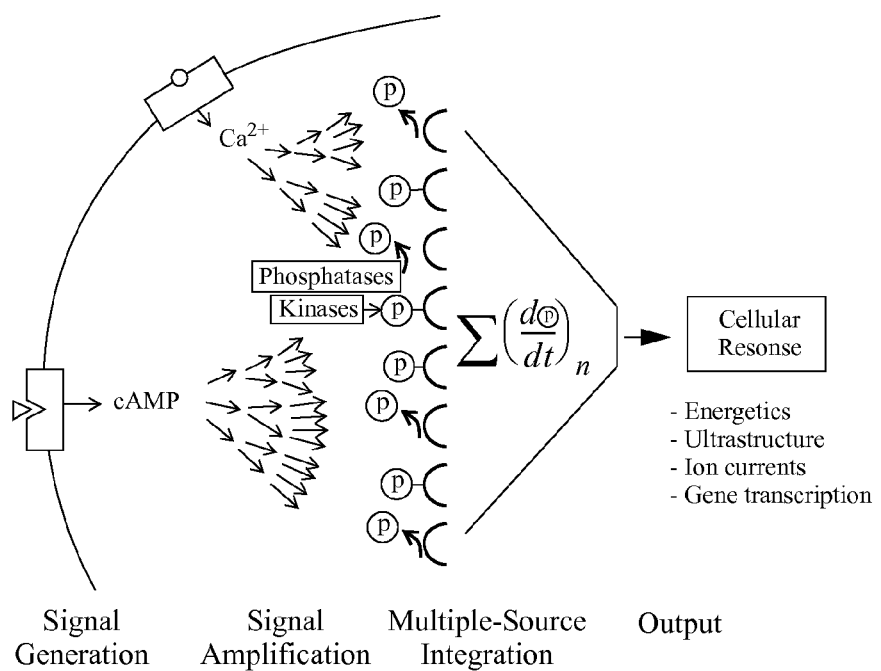
Figure 5b *(adapted from [Kindcai93])*

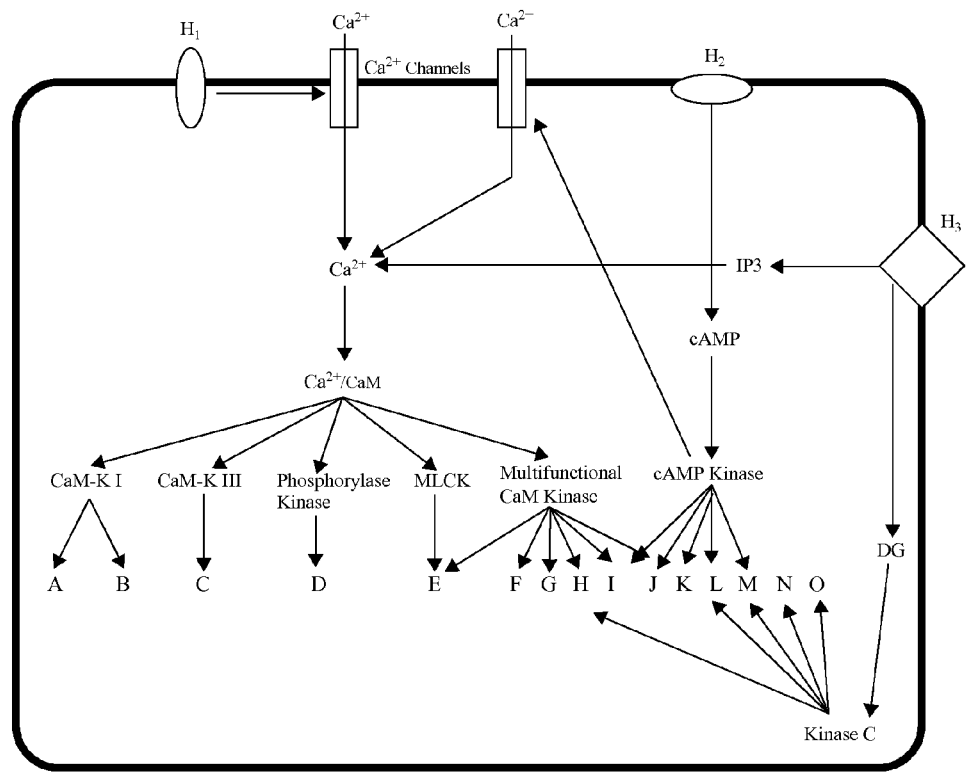
Figure 5c    *(adapted from [Shulma88])*
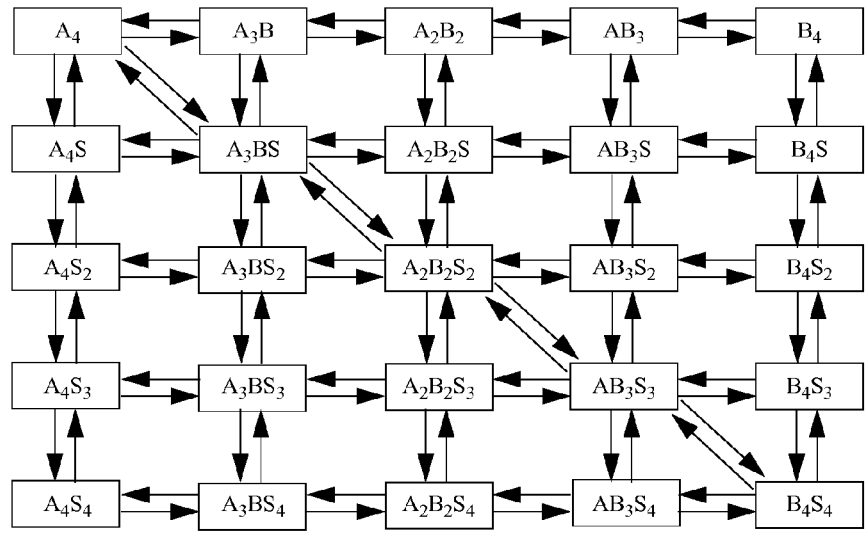
Figure 5d    *(adapted from [BucBuc68])*

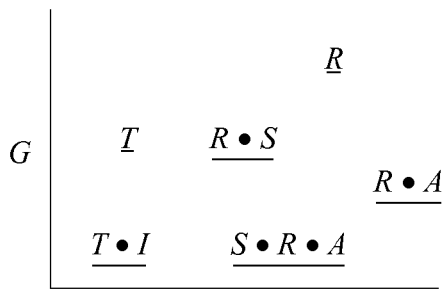
Figure 5e  *(adapted from [Traut07])*
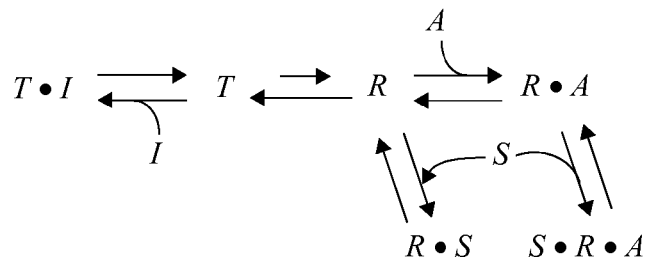
Figure 5f  *(adapted from [Traut07])*
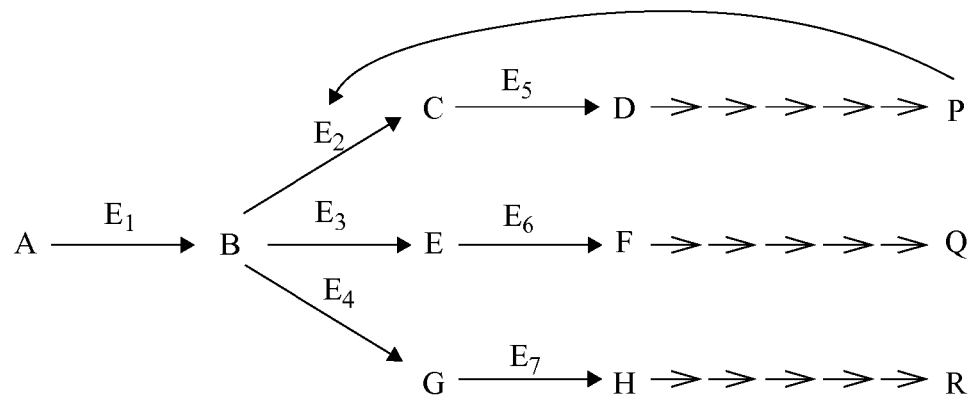
Figure 5g  *(adapted from [Traut07])*

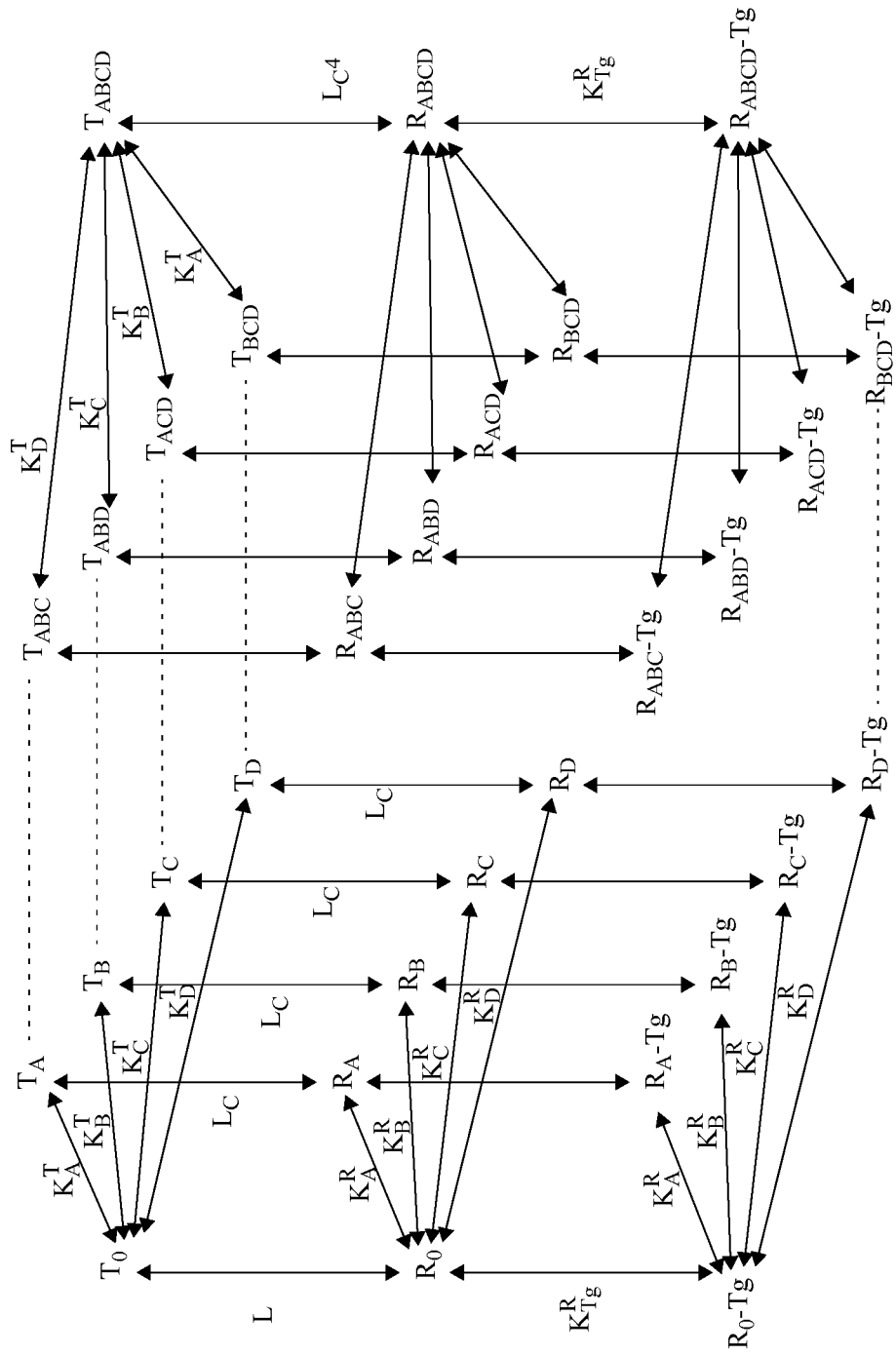
Figure 5h  (Adapted from [StElLe08])

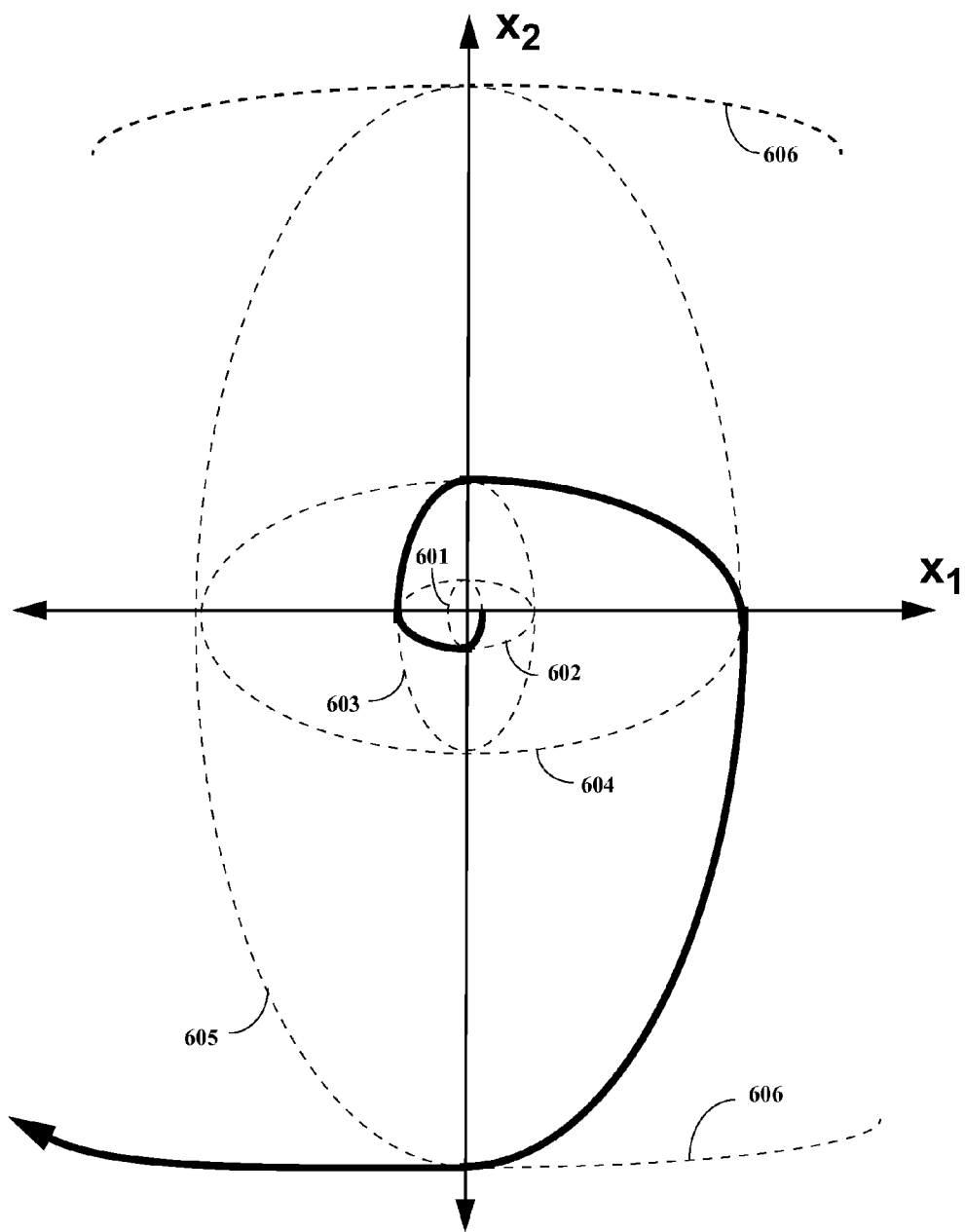
Figure 7a *(Adapted from [Ludwig 80] and [ThoTho78])*

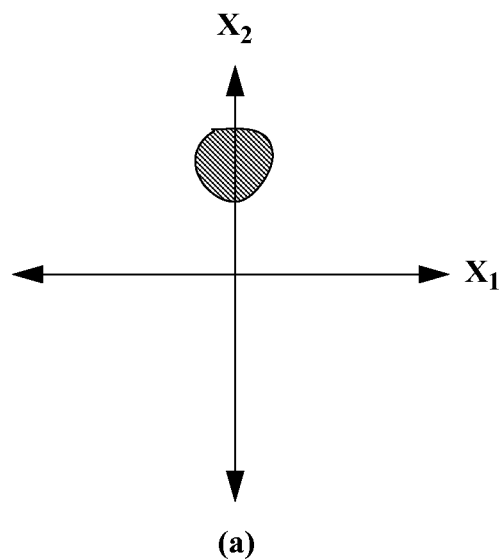
(a)
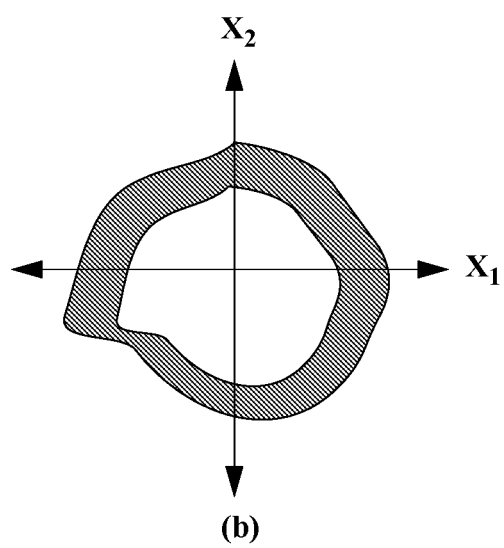
(b)
Figure 7b *(Adapted from [Brocke75])*

Instability
- Intermittent Behavior
- Failed Transmission
- Spurious Signals
- Unreliable Signaling Channel

NONLINEAR AND LIE ALGEBRA STRUCTURAL ANALYSIS SYSTEM FOR ENZYME CASCADES, METABOLIC SIGNAL TRANSDUCTION, SIGNALING PATHWAYS, CATALYTIC CHEMICAL REACTION NETWORKS, AND IMMUNOLOGY

CROSS-REFERENCE TO RELATED APPLICATIONS

This application claims benefit of priority of U.S. provisional application Ser. No. 61/214,643 filed on Apr. 26, 2009 and incorporates provisional application Ser. No. 61/214,643 herein.

BACKGROUND OF THE INVENTION

1. Field of the Invention

This invention relates to tools for computer modeling and information system tools for the study of the dynamic behavior—natural, desirable, undesirable, etc.—of wide ranges of chemical and biochemical reaction networks, such as signaling cascades, having nonlinear mathematical models (for example involving products of state variables and models of allosteric enzymes) and, particularly, to the creation of structured catalogs of known and hypothetical chemical reaction networks (including structured mathematical models), the creation of mathematical modeling tools targeted at uncovering 'hidden' behaviors suspected of said nonlinear mathematical models, and the use and interworking of these individually or in combination with one another and other external information, modeling, analysis, interactive, and presentation systems and methods.

The system and method herein can be applied to a wide range of life science applications, including disease research, metabolic research, and drug design as well as applications in nanotechnology, sensors, chemical computation, and chemical plant operation.

2. Background and Related Art

Over the last few decades there has been considerable increase in interest in signaling and signal transduction networks within biological systems. Study of these has yielded tremendous value in the understanding of disease, metabolism, drug discovering, DNA transcription, and a number of other areas. Future study appears to hold rich promise, as these basic frameworks of biochemical communication are involved in almost all aspects of life processes. Additionally, these biochemical communications channels—together with their implicit controlling and regulatory structures—can be adapted to great value in future nanotechnology systems, manufacturing, and other non-life-science applications.

Implicit in biological signaling and signal transduction are individual sequences of chemical reactions. Each of these sequences begins with a chemical reaction of one kind, which, as it progresses, subsequently initiates one or more chemical reactions of another kind. The latter reaction in turn would cause one or more additional types of subsequent reactions to occur, and so on, to form chain that can act as a chemical channel for carrying information. The typical links in the chain are the products produced in a given chemical reaction being such that they initiate the reaction that follows it. Because the information is carried by a stimulus being transformed by each reaction in the chain, the term "transduction" is applied, in analogy with transducers that transform an input optical, mechanical, electrical, or mechanical stimulus into an output stimulus of another type. Signaling occurs within cells, within substructures of cells, among cells, and can also occur organism-wide.

In naturally occurring biological systems, there are significant numbers of wide-ranging types of signaling and signal transduction communications channels. The coexistence and structured interactions of these form a network, hence the notion of signaling and signal transduction networks. A startling 20% (that is ⅕) of the coding genes in humans encode for proteins directly involved in signal transduction [Venter01]. Signaling and signaling pathology also occurs in plants and animals.

The constituent biochemical signaling and signal transductions in the environments where they occur are extraordinarily dependable, implementing or supporting almost every life process on the planet. However, biochemical signal transductions can sometimes go awry. Such signal transductions process failure has been explicitly linked to decease, illness, and pathology, including cancer. For example, dysregulation of the Signal Transducer and Activator of Transcription ("Stat") proteins, RAF kinase signaling pathways (such as Ras/RAF/MEK/ERK), cell cycle Cyclin-CDK complexes aspects of mitosis-promoting factors, growth factor roles in chemical signaling pathways, and many other signaling pathways have been implicated in cancer. A few of the many know or conjectured other examples of signaling pathways involved in disease can be found in the books [CarBri07], [BrCaMZ04], [Frank03], [Boyd91] and a host of articles publishing monthly worldwide.

These failures can result from variations in the ambient reaction environment or from unintended "cross talk" (coupling) between individual reactions in two or more biochemical signal transduction pathways (or even within the same pathway). Modes of failure and their behavior can be widely variant and remain poorly understood. It is to this, and a number of related problems and applications, that the present invention is directed.

More specifically, despite the extensive study of biochemical signal transductions the area remains poorly understood. Much effort and success has been made in identifying specific sequences of chemical reactions in specific metabolic and transcriptional pathways and the constituents of these. However, the internal structure of the specific reaction types are less understood and few dynamic behaviors have been reduced to representative mathematical models. Additionally, few of the reaction constants, which determine the dynamic behavior of the mathematical models, have been viably measured in ways relevant to their in situ occurrences.

Further, even for known mathematical models, the dynamics quite often comprise nonlinear differential equations. Few researchers can work well with these, and so often these nonlinear differential equations are linearized (removing their nonlinear character) and/or studied in steady-state equilibrium (setting all time derivatives to zero) therefore miss both the intrinsic nonlinearities and intrinsic dynamics. In other fields of study (such as electronic communications and dynamic control systems) involving nonlinear differential equations, it is through the detailed study of the nonlinear dynamics behavior that reveals essential aspects of instability, trajectory bifurcations, sensitivity to outside disturbances at specific points in the signal chain, and other key aspects relatively to questions of robustness and failure modes. It is additionally to this, and a number of other related problems and applications, that the present invention is directed.

Additionally, computer models exist for the numerical simulation of the dynamics of classical enzyme reactions. Most of these are directed to the kinetics of isolated enzyme reactions, although a few are directed towards enzyme cascades in particular. Although useful, these computer models do not provide structural stability analysis of the larger nonlinear enzyme cascade dynamics (as may be valuable for revealing essential aspects of instability, trajectory bifurcations, sensitivity to outside disturbances at specific points in the signal chain, and other key aspects relating to questions of robustness and failure modes).

Turing from reaction modeling specifically, attention is directed to the immensely active area of bioinformatics systems.

Bioinformatics systems are well known and have evolved from conventional database technologies to broader types of systems incorporating chemistry computations involve that involve knowledge representation, knowledge processing, symbolic computation, expert systems, predicate logic reasoning, machine learning, evolutionary computation, and neural network computation (see, e.g., [Schulze95]). These have a traditional orientation towards molecular structure, molecular topology, molecular typography, molecular classification schemes, amino acid sequencing, conformation and folding properties, chemical properties, receptor site characterization, and aspects of reaction graphs. Also there are a number of tools for modeling differential equations and chemical reactions.

Even as the field of bioinformatics is exploding, so is the expanding identification of metabolic signal transduction mechanisms involving enzyme cascades and other types of chemical reaction networks (for example, involving free metal ions such as calcium, sodium, and potassium, ions of chlorine, etc.). A large number of signaling transduction networks are known, most albeit in early identification, and are typically barely understood in isolation and even less understood in their broader intertwine operations and roles within the organism. Some of the complications include:

The poor understanding and characterization of the types of differential equations that naturally model most signal transduction processes, for example such as enzyme cascades. In particular, many signaling cascades involving catalytic multiplying effects which model as a multiplicative product between the concentration of two or more chemical species within or in ambience of the cascade. These equations are typically correctly identified, but then linearized, studied in equilibrium conditions (by setting all time derivatives equal to zero), partial equilibrium (setting fast-reaction derivatives equal to zero), or at best studied with numerically computed solutions in idealized, simplified settings.

The extensive opportunities for explicit "crosstalk" among signal transduction pathways, where one signaling transduction path's chemistry affects another signal transduction path, as well as situations where exogenous processes affect the ambient environment of the signal transduction path. The former of these, explicit crosstalk, is controversial as there are many more opportunities for it (analogies have been made to sloppy software "spaghetti code" resulting from eons of incremental chemical evolution) yet many arguments can be made as to signaling paths being so localized (for example, as is well appreciated in calcium signaling) that there is limited natural opportunity in living organisms for such signal transduction pathway crosstalk interference.

The limited understanding in both of these areas has further compounding concerns, for example:

The types of differential equations involved can be modeled as types of so-called 'bilinear control systems' which have had some study in the context of both engineering (electrical, chemical, and nuclear) and in abstract mathematics (involving Lie algebras of matrices). In even the limited understanding of those systems, a wide range of hidden and unexpected properties are possible, including several surprising modalities that lead to instabilities and wide deviation form quiescent behavior [Ludwig80], [Mohler73], some examples of which will be provided later.

Other types of nonlinear behavior, for example hysteresis, chemical chaos, chemical self-organization, etc. can emerge in these systems under certain quantifiable conditions.

Even if crosstalk and where situation where exogenous processes affect the ambient environment of the signal transduction path are relatively rare, the fact that a daily increasing number of metabolic problems and pathologies as well as drug design and analysis isolate variation and interference with signal transduction pathways make expanded understanding of this area still potentially quite valuable.

What would therefore appear to be an extremely valuable and useful tool in current and future metabolic and drug research for humans and animals, study and treatments of plant pathologies, design of chemical sensors and nanotechnologies, as well as potentially creating valuable new research directions, are systems and methods combining the following:

A structured catalog of signal transduction pathways, each including:
  structural mathematical models of the reaction dynamics;
  values of coefficients and parameters of these models;
  known related chemistry of the pathway's chemical constituents;
Mathematical tools for checking the structural behavior of these mathematical models, in particular designed to be operative for:
  Identification of internal proclivities towards instabilities;
  Identification of potential sensitivities to known and unknown candidate crosstalk processes;
  Identification of potential sensitivities to ambient chemical environments;
Ability to combine isolated models into a larger model which in turn can be checked in the manner above as the combined models (for example, those which crosstalk with one another) as the combined models will likely behave differently than the isolated models;
Ability to replace models or groups of models with other models or groups of models for various reason, such as but not limited to:
  Incorporation of improved models;
  Incorporation of more comprehensive models;
  Incorporation of simplified models;
  Incorporation of more isolated models;
  Incorporation of trial hypothetical models;
  Incorporation of perturbation(s) and/or control(s) into models;
  Naturally support evolution of models;
  Study of legacy models;
Provide a standardized framework, I/O handling, and variable handling for models for various reason, such as but not limited to:
  Exchange of models among groups of researchers;
  Provide for sale, licensing, and/or purchase of models.

In addition, the arrangement described above can be recast to address a broader range of chemical reaction networks, including non-biological ones, which to date have had limited development and tools [RodRod64], [TeZeBo96]. Such a recast arrangement could be particularly valuable in traditional technologies such as the design of controlled chemical reaction sequences in chemical plants, the design and operation of chemical plants themselves, and failure analysis of controlled chemical reaction sequences and chemical plants. Further, such a recast arrangement can facilitate new chemical-based information processing technologies that can be incorporated into or create entirely new types of chemical sensors and nanotechnology devices.

Further, as nanoscale technologies and other technology advances unite chemical reaction networks, supramolecular chemistry, conventional electronics, molecular electronics, optical-electronic processes, optical-chemical processes, small-scale mechanics, molecular computing, quantum computing, and other phenomenon, the invention can be expanded into a Computer-Aided Design ("CAD") tool for integrated multi-process dynamical design. This is a straightforward expansion of the invention as all that is required is an expansion of the type and number of mathematic models, catalog entries, and catalog fields.

SUMMARY OF THE INVENTION

In an aspect of the invention, a computer modeling system is implemented for study of behavior of complex signaling pathways comprising a computer representation of one or more nonlinear models of at least one signaling pathway arrangement involving enzyme cascades and/or allosteric enzymes and feedback.

In another aspect of the invention, the invention provides a structured catalog of signal transduction pathways.

Another aspect of the invention is the provision of mathematical tools for checking the structural behavior of a mathematical reaction dynamics model.

Another aspect of the invention is the provision for combining isolated models into a larger model which can be analyzed in the same manner as isolated signal transduction pathway dynamics.

Another aspect of the invention is for the structured catalog of signal transduction pathways to include information pertaining to structural mathematical models of the reaction dynamics.

Another aspect of the invention is for the structured catalog of signal transduction pathways to include information pertaining to values of coefficients and parameters of these models.

Another aspect of the invention is for the structured catalog of signal transduction pathways to include information pertaining to known related chemistry of the pathway's chemical constituents.

Another aspect of the invention is for the algorithmic tools checking the structural behavior of mathematical reaction models to be sensitive to and able to identify internal proclivities towards instabilities.

Another aspect of the invention is that the algorithmic tools for checking the structural behavior of mathematical reaction models include tests pertaining to Lie matrix algebras.

Another aspect of the invention is that the algorithmic tools for checking the structural behavior of mathematical reaction models include tests pertaining to Lie matrix algebras applied only to mathematical subspaces within the reaction dynamical state space.

Another aspect of the invention is that the algorithmic tools for checking the structural behavior of mathematical reaction models include tests pertaining to the mathematical graph associated with matrices describing the reaction dynamics.

Another aspect of the invention is that the algorithmic tools for checking the structural behavior of mathematical reaction models include tests pertaining to matroids associated with matrices describing the reaction dynamics.

Another aspect of the invention is that the algorithmic tools for checking the structural behavior of mathematical reaction models include provisions for additional tests to be added as the theory becomes available.

Another aspect of the invention is that the algorithmic tools for checking the structural behavior of mathematical reaction models be structured in a modular fashion.

Another aspect of the invention is providing for the algorithmic tools checking the structural behavior of mathematical reaction models to be sensitive to and able to identify potential sensitivities to known and unknown candidate crosstalk processes.

Another aspect of the invention is providing algorithmic tools checking the structural behavior of mathematical reaction models to be sensitive to identification of potential sensitivities to ambient chemical environments.

Another aspect of the invention is providing algorithmic tools for characterizing the presence and effects of hysteresis processes in the mathematical models.

Another aspect of the invention is providing algorithmic tools for introducing the effects of hysteresis processes in the mathematical models, for example, as can be resultant from folding variations, tautomeric transformations, etc. of chemical species.

Another aspect of the invention is providing for adaptations pertaining to identifying yet unknown potential crosstalk processes for future laboratory study.

Another aspect of the invention is providing for adaptations pertaining to drug design.

Another aspect of the invention is providing for adaptations pertaining to immunological systems with mathematical models that comprise bilinear matrix differential equations.

Another aspect of the invention is providing for adaptations pertaining to more general forms of chemical reaction networks.

Another aspect of the invention is providing for adaptations pertaining to the design of controlled chemical synthesis.

Another aspect of the invention is providing for adaptations pertaining to the operation of controlled chemical synthesis.

Another aspect of the invention is providing for adaptations pertaining to the failure analysis of controlled chemical synthesis.

One familiar with the art will appreciate that the invention has many additional aspects beyond those stated above.

BRIEF DESCRIPTION OF THE DRAWINGS

The above and other aspects, features and advantages of the present invention will become more apparent upon consideration of the following description of preferred embodiments taken in conjunction with the accompanying drawing figures, wherein:

FIG. 1a (adapted from [BaMiZi75]) illustrates a pictorial depiction of a simple abstract multiple-level enzyme cascade.

FIG. 1b (adapted from [HeNeRa02]) shows more complete detail of how such simple signaling structures are manifest in actual sequential signaling cascades.

FIG. 2a (from [PfScMS95]) shows exemplary linear chemical signal amplification processes.

FIG. 2b (from [PfScMS95]) shows exemplary nonlinear chemical signal amplification processes.

FIG. 3a (adapted from [Roach77]) depicts situations where the principle interest lies with open loop gains.

FIG. 3b (adapted from [StaCho78]) depicts enormous multistage amplification effects.

FIG. 3c (adapted from [VarHav90]) depicts the dynamics of rise times of various species within the cascade reactions.

FIG. 4a depicts an exemplary regulatory interplay in a broader exemplary enzyme cascade (E1, E2, E3, EI4) environment with various initiators and inhibitors (I1, I2, I3, I4, I5, I6) (adapted and modified from [Roach 1977]).

FIG. 4b shows a depiction of multiplicative "variable gain" control view of enzyme concentrations in a signaling cascade.

FIG. 4c shows a more general depiction of a multiplicative operation between an incoming (bio)chemical signal $Y_{in}$ and a function $f(\cdot)$ of a modulating (bio)chemical signal $X_{mod}$ that determines the magnitude of the value of an incoming (bio)chemical signal $Z_{out}$.

FIG. 5a (adapted from [Saunder05]) depicts an exemplary catalog of cell calcium signaling calling out calcium ions, sodium ions, receptors ion stores, tubules, membranes, exchangers, and (implied by geometry) localization structures.

FIG. 5b depicts interactions of calcium with elements depicted in FIG. 5a as well as signal generation, signal amplification, multiple-source signal integration, and outputs directing cellular response.

FIG. 5c (adapted from [Shulma88]) depicts a pathway representation calling out specific types of enzymes and the role of calmodulin.

FIG. 5d (adapted from [BucBuc68]) depicts a discrete state-transition representation of the "concerted transition" model of Monod and Koshland for a representative tetramer allosteric enzyme comprising four identical protomers with two locally conformational states, each having different affinities for an effector ion or ligand S.

FIG. 5e (adapted from [Traut07]) depicts a free energy (G) plot for an exemplary enzyme conformation of the active ("tense" or T) and inactive ("relaxed" or R) conformations of the ternary enzyme protein folding as they interact with a substrate (S), activator (A), and inhibitor (I).

FIG. 5f (adapted from [Traut07]) depicts the organization of these state transitions.

FIG. 5g (adapted from [Traut07]) depicts an exemplary branched cascade arrangement, showing an exemplary feedback path closing one of the branches, that can result from an enzyme and which apply to various states of allosteric enzymes.

FIG. 5h (adapted from [StElLe08]) depicts a postulated model for a detailed treatment of calmodulin behavior in a cascade.

FIG. 7a (adapted from [ThoTho78], also in [Ludwig80]) depicts a parameterized stable elliptical trajectory with axis of eccentricity rotated by a small bounded periodic control variation can be "pumped" into unbounded instability.

FIG. 7b depicts an example of a reachable set of points within the reach of the system dynamics that begins with a convex connected region but evolves to include a hole, thus defining forbidden states.

DETAILED DESCRIPTION OF THE PREFERRED EMBODIMENTS

Figure 6A:
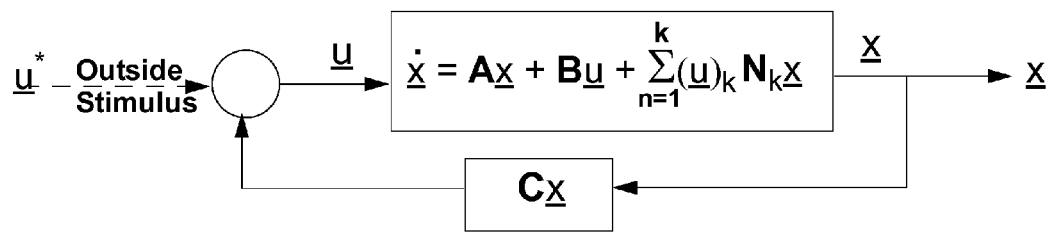
FIG. 6a shows an illustration of a bilinear system with both linear and bilinear forms of state variable feedback, i.e., the arrangement from system science that shares mathematical description with several classes of chemical and signal transduction cascades.

In the following description, reference is made to the accompanying drawing figures which form a part hereof, and which show by way of illustration specific embodiments of the invention. It is to be understood by those of ordinary skill in this technological field that other embodiments can be utilized, and structural, algorithmic, architectural, as well as procedural changes can be made without departing from the scope of the present invention.

The invention will be developed first in the context of a tool for the study of enzyme cascades, and then will be expanded to more general types of signal transduction cascades. The scope of the invention readily extends to more general chemical reaction networks, and from this as a tool for the design, operation, and failure analysis of sequential chemical reactions. Additionally, the scope of the invention can be expanded into a CAD tool for integrated multi-process dynamical design spanning any two or more of chemical reaction networks involving sequences of catalytic processes or other mathematically related processes.

In enzyme cascades and other types of biochemical signaling transduction pathways, variations in the concentration of one chemical species act as a "control" which creates variations in the concentration of another "controlled" chemical species. In many cases, the variations of the "control" and "controlled" are of similar magnitude. In many other cases, particularly those involving kinase, other enzymes, or other catalytic processes, each newly available molecule of the "control" species acts catalytically to repeatedly create molecules of the second species. The result is a multiplying or cascading effect, similar to the amplification process in electrical circuits (and at times referred to as such [Levine66], [PfScMS95]). Signal attenuation ("damping") can also occur [HeNeRa02]. FIG. 1a (adapted from [BaMiZi75]) illustrates a pictorial depiction of a simple abstract multiple-level enzyme cascade with, at the $i^{th}$ level, a substrate compound $S_i$ acted upon by an enzyme $E_i$ to form a product compound $P_i$; the product at level n in fact the enzyme of level n+1, thus forming the cascade.

FIG. 1b (adapted from [HeNeRa02]) shows more complete detail of how such simple signaling structures are manifest in actual sequential signaling cascades (for example the presence of growth factors such as EGF, PDGF, or NGF stimulating a receptor tyrosine kinase leading in turn to the sequential activation of various downstream kinases), ultimately resulting in a metabolic response. Most signaling cascades are considerably more complicated, as will be discussed. A number of signaling cascades match the model, varying in the resultant products $P(X_i)$ and reaction rates $\alpha_i$ and $\beta_i$.

In some situations the function served can effectively be a conversion from one type of chemical signal chemistry to another and the cascade step can keep the effective signal level constant by matching the source and product concentrations exactly. In many cases, however, a signaling cascade step invoke amplification or dampening (attenuation). FIG. 2a (from [PfScMS95]) shows exemplary linear (a) and non-linear (b) chemical signal amplification processes. FIG. 2b (from [PfScMS95]) shows exemplary nonlinear chemical signal amplification processes.

For study of cascades where the isolated open-loop signal transduction is the principal concern, one would be concerned with open loop gains, as depicted in FIG. 3a (adapted from [Roach77]), the enormous multistage amplification effects as depicted in FIG. 3b (adapted from [StaCho78]), and the dynamics of rise times of various species within the cascade reactions as depicted in FIG. 3c (from [VarHav90]).

Inhibitors can interact in a cascade step (for example, employing an allosteric enzyme, to be discussed shortly) to reduce or block the signal propagation through the signaling cascade. Additionally, a downstream step in a signaling cascade can also serve as an initiator for a signal that can subsequently propagate through the rest of the cascade without a signal from upstream. Further, one or more of the signaling cascade steps may have their individual actions modulated (increased or decreased) by various forms of other metabolic controls. FIG. 4a summarizes these by depicting an exemplary regulatory interplay in a broader exemplary enzyme cascade (E1, E2, E3, EI4) environment with various initiators and inhibitors (I1, I2, I3, I4, I5, I6) (adapted and modified from [Roach 1977]).

In mathematically modeling the dynamics of such systems, a separate "state" variable is typically used to represent the concentration of each relevant chemical species (see for example [MesTak75, [Bose82], or [Wiberg71] for general background on state variable models). Most of the available theory for state variable models relate to linear systems of differential equations. Among other things this rich theory provides for the reduction of high-order linear differential equations into a collection of multivariable first-order differential equations which can be then represented as matrix operations on multidimensional "state vectors."

The class of enzyme cascades described above require a more involved type of model, specifically one involving multiplying operations among the values of the concentration levels of enzymes or other (bio)chemical constituents. In such a model, the multiplying operations among enzyme (or other catalysts) mathematically lead to one state variable to multiply another. This is similar to having one state variable in an electrical circuit control the amplifying gain applied to another state variable. FIG. 4b shows a depiction of such a multiplicative operation, although typically there is a multiplicative scaling constant of some sort. It is noted that similar types of "variable gain" control methods are employed in a wide range of electronic, mechanical, and numerical man-made systems ranging from adaptive systems to automatic gain controls widely used in audio, video, photography, and communications.

In particular, at a step in a signaling cascade the presence of specific enzymes or other substances inhibiting or activating substances can act a "molecular switch" (for example, see [Bluthg01]) gating the propagation of signaling pathways or signaling events through the cascade. It is noted for later mathematical modeling considerations that such a molecular switch can be viewed as a type of amplification with a gain that takes on either zero or non-zero values. Thus, both modulation and molecular switch cases involve multiplication operations within processes affecting the concentration of one or more reaction products.

Additionally, allosteric enzymes (and other allosteric processes, both to be considered in more detail below) also introduce a controlled scaling ("modulation") operation that can be represented as a multiplicative operation responsive to a function of an incoming (bio)chemical signal. FIG. 4c shows a more general depiction of a multiplicative operation between an incoming (bio)chemical signal $Y_{in}$ and a function $f(\cdot)$ of a modulating (bio)chemical signal $X_{mod}$ that determines the magnitude of the value of an incoming (bio)chemical signal $Z_{out}$. For linear modulation $f(\cdot)$ is a linear function, while for models of molecular switches and allosteric enzymes $f(\cdot)$ is a nonlinear function and may include other features such as hysteresis, step behavior, etc.

In addition to enzymes, signaling can employ other constituents, for example any from the (somewhat overlapping) list of hormones, cytokines, growth factors, ion channels, ligands, as well as receptors. For example, FIG. 5a (adapted from [Saunder05]) depicts an exemplary catalog of cell calcium signaling, calling out calcium ions, sodium ions, and receptors as well as other structures such as ion stores, tubules, membranes, exchangers, and (implied by geometry) structures providing pathway localization giving crosstalk isolation and limiting the quantity of calcium ions required for signaling. The hormones, cytokines, growth factors, ion channels, ligands, and receptors interact with enzymes and enzyme cascades in a signaling pathway, as shown in FIG. 5*b* (adapted from [Kincaid93]). The hormones, cytokines, growth factors, ion channels, ligands, and receptors, among others, provide a means for signaling among cells and regional or global metabolic control by other aspects and elements of an organism and/or the environment.

FIG. 5*b* also depicts higher level functions involved with and/or provided by signaling pathways and cascades in general such as signal generation, signal amplification, multiple-source signal integration, and outputs directing cellular response. FIG. 5*c* (adapted from [Shulma88]) depicts a functional pathway representation calling out specific types of enzymes and the role of calmodulin.

Calmodulin provides a specific example of two additional aspects important to many signaling transduction networks and signaling cascades. The first of these (mentioned several times) is that of crosstalk. Calmodulin is a component in an extremely large number of independent pathways involving calcium signaling (as suggested in FIG. 5*c*). These are typically isolated by various schemes and arrangements involving spatial segregation, temporal segregation, and frequency modulation of calcium ion concentrations, among others. Nonetheless, there can be opportunities for crosstalk and related disturbances among these otherwise independent pathways involving calcium signaling. Additionally, important calmodulin is known to naturally crosstalk with important Protein Kinase C [MacSch92] [Shmitz98], and thus there could easily be yet-to-be-discovered pathological crosstalk mechanisms as well between these key and central enzymes as well.

A second aspect of calmodulin is as an apparent allosteric enzyme. Allosteric enzymes provide an important modulation element for signaling cascades and pathways. Typically allosteric enzymes have two or more (often four) binding sites, and the number of bound and unbound sites determine the affinity of the enzyme for further reactions as part of a signaling cascade or pathway. The mechanism involved is typically related to conformational changes in the enzyme protein as each binding occurs. FIG. 5*d* (adapted from [BucBuc68]) depicts a discrete state-transition representation of the "concerted transition" model of Monod and Koshland for a representative tetramer allosteric enzyme comprising four identical protomers with two locally conformational states, each having different affinities for an effector ion or ligand S. Such models can be created from empirical measurements, but importantly they can also be rendered by minimal-energy analytical models of the enzyme's conformational changes. FIG. 5*e* (adapted from [Traut07]) depicts a free energy (G) plot for an exemplary enzyme conformation of the active ("tense" or T) and inactive ("relaxed" or R) conformations of the ternary enzyme protein folding as they interact with a substrate (S), activator (A), and inhibitor (I). FIG. 5*f* (adapted from [Traut07]) depicts the organization of these state transitions. These are readily modeled by computer algorithms.

FIG. 5*g* (adapted from [Traut07]) depicts an exemplary branched cascade arrangement, showing an exemplary feedback path closing one of the branches, that can result from an enzyme and which apply to various states of allosteric enzymes. This offers an initial hint at the types and degrees of complexity inherent in signaling pathways and signaling cascades, and specifically at the need for a computer tool so that these complex interactions among cascades can be studied. New feedback loops, new steps and elements of cascades, and new modulations of them are being discovered and reported every few days as research and understanding intensifies, yet to date the even the surface of this area has barely been surveyed. Further regarding allosteric enzymes complexity and calmodulin in particular, FIG. 5*h* (adapted from [StElLe08]) depicts a postulated model for a detailed treatment of calmodulin behavior in a cascade, This model turns out to very accurately match empirical measurements that had otherwise been unexplained and also directly matches what would be expected from the ternary enzyme protein folding structure of the calmodulin molecule. This example demonstrates the radically increasing complexity handling needed (this is just one element in a cascade which in turn is often multiply-branched and surrounded various feedback loops), again motivating the essential need for a computer tool. This example also demonstrates the value for introducing a model transcendent of specific structural study, a function that can be provided by a computer tool as provided for by the invention.

Additionally, this example [StElLe08] further demonstrates how quickly aspects that were entirely unknown (here regarding calmodulin, the classic central enzyme of calcium signaling) can emerge and need to become incorporated into many existing models, suggesting the need for a modular interface to accept replacement as well as entirely new models, as is provided for by the present invention. Another motivating example can be found in [Robubi08] where after a Ras/RAF/MEK/ERK kinase signaling model without feedback had been long standing, a feedback loop was recently discovered and incorporated in the mathematical model. Additionally, the resulting mathematical model was used to demonstrate detailed behavior of a tumor-suppressing drug. Here again, the need for an ability to amend mathematical models that may be long-standing is demonstrated, as well as the value of these models in drug and therapy discovery. These are provided for by the invention.

Regarding mathematical modeling modulation and cascades suitable for implementation in a computer algorithm, the most directly honest way of representing the dynamics of systems where one state variable controls the gain of another state variable in affecting the rate of change of a third state variable, the result is a system of differential equations with "cross products" among the state variables. This has been repeatedly recognized in many papers on mathematical models of the dynamics of enzyme cascades (see [Breire07] as one example). In general the detailed dynamics a number of comprise nonlinear differential equations, most involving such cross-product terms among state variable. Few researchers can work well with these, or nonlinear differential equations in general, so usually (as in Breire07], [BinHei02], and countless others) these nonlinear differential equations are linearized (removing their nonlinear character) and/or studied in steady-state equilibrium (setting all time derivatives to zero) therefore miss both the intrinsic nonlinearities and intrinsic dynamics. In other fields of study (such as mechanical systems and dynamic control systems) involving nonlinear differential equations, it is through the detailed study of the nonlinear dynamics behavior that reveals essential aspects of instability, trajectory bifurcations, sensitivity to outside disturbances at specific points in the signal chain, and other key aspects relatively to questions of robustness and failure modes.

Feedback loops further complicate the picture [Bluthg02], as does allosteric enzymes, multiple pathways, and crosstalk mingling among the signaling pathways and cascades. It is specifically to characterizing and studying the effects of these that other higher-order algebraic properties of differential equation models of metabolic enzyme cascades can be useful, as provided for by the invention via algorithmic implementation and a user environment. The paper [BinHei02] attempts to characterize some stability effects of crosstalk effects using gross properties of graph and matroid structures within the matrix arising from linearization of the signaling cascade differential equations. This course of research is noteworthy and in keeping with notion of "hidden" structural stability implications, but suffers from linearization step throwing out all multiplicative structure among state variables.

Connection with Bilinear Control Systems

In 1975 Banks, Miech, and Zinberg [BaMiZi75] showed that these systems can be modeled as "bilinear control systems" in the presence of feedback. By definition, linear control systems relate rates of change of state variables to linear combinations of the state variables and externally adjusted control variables:

$$dx/dt = Ax + Bu \quad (1)$$

where x is the vector of state variables and u is a vector of control variables.

By definition, bilinear control systems additionally relate the rates of change of state variables to cross-products of state variables with externally adjusted control variables:

$$d\underline{x}/dt = A\underline{x} + B\underline{u} + \text{sum over } k[(\underline{u})_k N_k \underline{x}] \quad (2)$$
$$\text{linear} \quad \text{linear} \quad \text{bilinear}$$
$$\text{dynamics} \quad \text{control} \quad \text{control}$$

where (u)k denotes the $k^{th}$ component of the vector u.

Both linear and bilinear control systems are typically studied in the presence of linear state variable feedback, i.e., where the control variables are linear combinations of the state variables:

$$\underline{u} = C\underline{x} \quad (3)$$

where (Cx)k denotes the $k^{th}$ component of the vector Cx.

Thus, in the presence of linear state variable feedback, the cross-products of state variables with such control variables become cross products among pairs of state variables:

$$d\underline{x}/dt = A\underline{x} + BC\underline{x} + \text{sum over } k[(C\underline{x})_k N_k \underline{x}] \quad (4)$$
$$\text{original} \quad \text{shift} \quad \text{in cross-products}$$
$$\text{linear} \quad \text{linear} \quad \text{in} \quad \text{state}$$
$$\text{dynamics} \quad \text{dynamics} \quad \text{variables}$$

The new linear components of the dynamics are shifted from the linear operator (matrix) A to the linear operator (matrix) [A+BC]. FIG. 6a shows an illustration of a bilinear system with both linear and bilinear forms of state variable feedback, i.e., the arrangement from system science that shares mathematical description with several classes of chemical and signal transduction cascades.

Bilinear systems in general and bilinear control systems in particular have a number of special useful and calculable properties (see for example [AgaGaj95], [Brocke75], [Mohler73]). However, little if any follow-on study using the bilinear system framework appears to be available, and the relation with bilinear systems called out by the relatively obscure paper [BaMiZi75] of Banks, Miech, and Zinberg seems to have been essentially forgotten. There are probably a number of potential reasons for this:

The specialty and often non-standard mathematical complexity typically inherent bilinear systems.

Development of most of the theory has been in the context of engineering (electrical, nuclear, mechanical).

Linear state variable feedback must be included for a bilinear system to attain the cross-products among the state variables.

The utility of the bilinear system in this context seems like an observational artifact and not particularly useful.

Larger scale aspects of the chemical dynamics involving complex reaction loops and signaling cross-talk were not as appreciated as they are today.

The vast discoveries and expanded understanding in signal transduction have largely occurred a generation apart from this time, circa 1975, when the ships of enzyme cascades and bilinear systems briefly "passed in the night."

However, putting the bilinear system situation aside, there is in fact a large important absence of the study of the dynamic behavior that results from these core intrinsic structures involving cross-products among the state variables, particularly in cases involving complex reaction loops and potentials for signaling cross-talk. In fact, many of the very papers which explicitly identify the cross-product of state variables structure proceed to then examine either linearized versions of the dynamic models or equilibrium conditions, i.e. with time derivatives of the dynamical system equations set to zero (for example, [BinHei02]). Even the 1975 paper of Banks, Miech, and Zinberg [BaMiZi75] which called out the parallels with bilinear control systems makes a number of simplifying assumptions (rapid equilibrium of faster reaction equations, linerization, assumptions about inhibitive processes, etc.). Other efforts study the stability of the equation systems using high-level Lyapunov techniques which can provide selective broad classes of stability results but require the informed trial-and-error identification of a viable Lyapunov and its successful application to an equilibrium point [KraBre63]. The resulting situation thus amounts to the following:

Tools available for deeper understanding of the dynamics of bilinear systems have been largely unused in the study of signaling transduction networks and metabolic enzyme/kinase cascades;

In fact it is largely the equilibrium conditions or straightforward Lyapunov characterizations that are available.

These compromised approaches perpetuate the lack of understanding of the dynamics of signaling transduction networks and metabolic enzyme/kinase cascades. This is unfortunate as life process in healthy stasis or progressive degradation is in fact:

a non-equilibrium condition;

involves dynamics with considerable structural detail yet with many properties cannot be revealed by classical techniques.

For study of cascades where the isolated forward open-loop signal transduction is the principal concern, the relation with bilinear systems is likely of limited consequence. In these situations one would be concerned with open loop gains, as depicted in FIG. 3a (adapted from [Roach77]), the enormous multistage amplification effects as depicted in FIG. 3b (adapted from [StaCho78]), and the dynamics of rise times of various species within the cascade reactions as depicted in FIG. 3c (from [VarHav90]).

In the current research environment, however, a more extensive understanding is becoming increasing indispensable. Enzyme recovery dynamics, feedback loops, exogenous regulatory controls, and signaling cross-talk transform open-loop cascade dynamics into considerably complex form whose pathological behavior and sensitivities are barely understood. It is in this setting in particular that the mathematical knowledge of bilinear control systems and the theoretic and computational tools used to examine their behavior can shed important light on matters of stability and sensitivities.

Computer Tool Components for Study of Algebraic Structure of Signaling Networks

In an embodiment the invention comprises a computer tool for the study of algebraic structure of signaling networks. This computer tool can be combined with numerical simulation tools. Such numerical simulations can use incorporations and/or adaptations of existing numerical simulation tools, such as Gepasi (and its extensions and progeny) [Mendes01] and Monod [SGMBE03], would preferably uses the numerical framework taught later in this patent specification. In an embodiment, at least some of the numerical simulation calculations are performed in algorithms that implement the mathematical constructions for consecutive chemical reactions taught in [RodRod64]. Additionally, various embodiments include steady-state equilibrium-condition tools implementing methods such as Elementary Mode Analysis [PSPKSP04], Extreme Pathways [PRPWP03], Flux Balance Analysis [SKBSG02], etc.

The invention provides for a wide range of components and/or utilities for algebraic structure of signaling networks including but not limited to:
  Lie algebraic methods (such as those described above and below);
  Flux cone analysis [LarBoc09];
  Algebraic graph/matroid analysis [Murota87] [KocHei08].

Lie Algebraic Structural Analysis

Figure 6B:
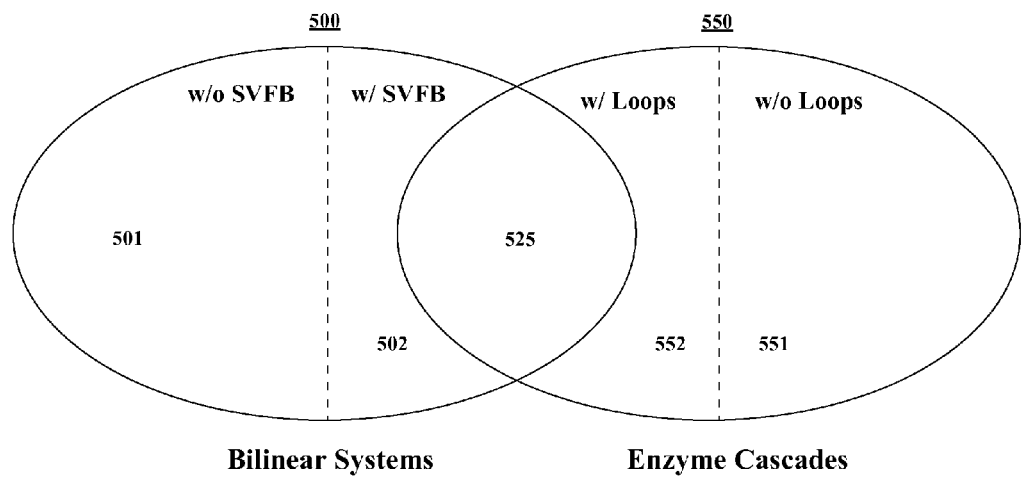
FIG. 6b shows a Venn diagram relating classes of bilinear systems with classes and various classes of signaling cascades.

FIG. 6b shows a Venn diagram relating classes of bilinear systems with classes and various classes of signaling cascades based on the discussion thus far. Of particular interest and potential value is the area of overlap among bilinear systems with state variable feedback and enzyme cascades with state variable feedback (SVFB) loops, exogenous regulatory controls, and signaling cross-talk. The invention provides for bilinear feedback control system tools directed to characterizing the dynamics and sensitivities of enzyme cascades containing feedback loops, exogenous regulatory controls, or potentially exposed to signaling cross-talk. As motivation some illustrative examples of the dynamics of bilinear systems with state variable feedback are provided below.

Among the many unusual properties of systems with bilinear structure are "hidden" means of instability resulting from small variation in control variables. An illustrative example from ([ThoTho78], reproduced in [Ludwig80]) is one where a stable elliptical trajectory with axis of eccentricity is rotated by a small bounded periodic control variation can be "pumped" into unbounded instability as shown in FIG. 7a.

Another noteworthy behavior is the structure of reachable sets. Brockett [Brocke75] provides an example of a reachable set of points within the reach of the system dynamics that begins with a convex connected region but evolves to include a hole, thus defining forbidden states, as illustrated in FIG. 7b.

Either of these two phenomena could represent either normal or abnormal conditions of a closed loop cascade or other complicated cascade. Many other examples of other types of exemplary unusual behavior and instabilities (including in fact periodic behavior in bilinear-structured metabolic enzyme catalyzed reaction systems [Walter73] and other bilinear systems [ZhaChe99], are available in the literature (see for example [Mohler73] and [Brocke75]), although there is no known comprehensive catalog of all possible behaviors as there is for strictly linear systems of differential equations). Some behaviors can be demonstrated which are apparently not available in the literature, for example types of hysteresis as has appears to have been demonstrated by the inventor [LudwigTA].

Of noteworthy interest are high order algebraic structures within bilinear dynamics that are explicitly connected to stability of the solutions and behavior of these differential equations. There is nothing like these within the stability properties of systems of linear differential equations. Thus the studies that linearize enzyme cascade differential equations with simplifying assumptions or only examine equilibrium conditions completely miss these hidden stability criteria, as well as the unique and surprising behaviors inherent in these types of differential equations.

An important specific example is the existence of a so-called transitivity conditions ([Booth75], [Ludwig80]) in Lie semi-simple algebras arising from portions or the entirety of the bilinear systems matrix operators A, B and $N_k$ (see Section 2 above for the role of these matrices). If these conditions are satisfied, then a disturbance of even a small size can drive a bilinear system over time to any state, thus revealing structural instabilities with respect to variations and disturbances. These results have a complicated history, but include a lineage starting with Caratheodary on to Chow's Theorem [Chow39] and further refined by Kucera [Kucera67], Ellliot, Tarn, and Cheng ([ChTaEl75], [Elliot71]), Sussman [Sussma76] and Brockett [Brocke73]. The later few of these, along with Ludwig [Ludwig80], and others restructured the Lie semisimiple algebra transitivity results developed by Kucera [Kucera67] into the formulations relating to bilinear systems. This includes a number of simple algorithmic tests on the matrices of a bilinear system to definitively determine the presence of the Lie semisimple algebra transitivity. [Ludwig80] showed the instability of the pumping instability example illustrated in FIG. 7a was predicted by these tests, and further developed additional tests for smaller substructures within larger-scale bilinear systems ("block subcontrollability"). Further as to the algorithmic aspects of these tests, Boothby [Boothb75] was able to exhaustively identify all classes of Lie semisimple algebras with transitivity. Thus there is a rich algorithmic environment for making structural tests for this "hidden" class of instability given the bilinear systems representing enzyme cascades.

Algorithms for this transitivity test as provided for by the invention, but can be directly implemented from the following (as provided in [Ludwig80]). The vector differential equation:

$$\dot{\underline{x}} = (A u + B v) \underline{x}$$

with scalar controls u,v is completely bang-bang controllable (u,v piecewise ±1) on $R_0^n$ iff the Lie matrix algebra generated by A and B, notated $\overline{L(A,B)}$, is transitive on $R_0^n$. Transitivity of the Lie matrix algebra $\overline{L(A,B)}$ can be determined in various computational ways, including as follows.

It is possible to generate every element in the linear basis of L(A,B) by exhaustively applying the Lie bracket operation $[\overline{M_1}, \overline{M_2}] = M_1 M_2 - M_2 M_1$, a finite number of times. A dimension argument shows that as the Lie group is of dimension $n^2$ the linear basis of L(A,B) contains at most $n^2$ matrices (as a result of the correspondence between the Lie group and Lie sub-algebra). Thus the basis can be found by computing the tree of sets $$F_{i+1} = \{[\underline{A}, \underline{X}], [\underline{B}, \underline{X}]\}$$

where $$F_0 = \{\underline{A}, \underline{B}\}.$$

Then $F_1=\{[A,B]\}$, $F_2=\{[A,[A,B]],[B,[A,B]]\}$, etc., which can be iteratively constructed by a computer algorithm computationally.

The resulting tree of sets can be tested in at least the following two ways in so as to establish transitivity of the Lie matrix algebra $L(A,B)$:

If the concatenation of linear basis elements of $L(A,B)$ is of rank n, then $L(A,B)$ is transitive. (Mathematically, if $\{c_i\}^m$, (with $m \le n^2$) is a linear basis for $L(A,B)$, then $L(A,B)$ is transitive if $p(c_1 x, \ldots, c_m x) = n \forall x \in R_0^n$). Such a rank test is readily implemented by a computer algorithm.

All Lie sub-algebras exhibiting transitivity of the natural linear action on $R_0^n$ have been exhaustively tabulated by Boothby. A test comparing $L(A,B)$ to the exhaustive Boothby tabulation can be implemented by a computer algorithm.

These tests provide "yes/no" results for this class of instability. Additional results as to the properties of small deviations from the conditions satisfying these strict Lie semi-simiple algebra transitivity tests could be incorporated and used to address, for example:

What happens as a metabolic enzyme or signaling cascade environment, for any number of reasons, drifts from a stable case towards this class of hidden instability?

Are some metabolic enzyme cascades more immune or susceptible to being thrown out of nominal behavior by crosstalk or shifts in the ambient chemical environment?

The fact that metabolic enzyme cascade systems work fine in most instances but then degrade under various conditions could easily be due to shifts in reactivity or crosstalk. Using analysis described could study how these could be manifest in systems that degrade. In particular, these types of studies could identify areas to search for in future biochemical study. Because the bilinear systems describing metabolic enzyme cascades have special variational and instability properties that can arise from small variations and disturbances, work here could explain phenomena that are not yet understood in the degradation of these systems because to date researchers may have only been looking for other mechanisms entirely, or observing only gross effects rather that this rich hidden structure.

Additionally, it is noted that bilinear feedback system representations have also been identified in the modeling various of immunology (for example, [Mohler79] [BrGiKS75] among others). The invention therefore provides for applications in immunology analysis and related aspects of drug design and disease study.

Flux Cone Algebraic Structural Analysis

Larhlimi and Bockmayr [LarBoc09] have developed a method determined by the network that yields a complete structured description of the steady-state flux cone through the network employing an "outer description" of the flux cone based on sets of non-negativity constraints. Reversible and irreversible reactions can be partitioned directly from this representation, directly providing a biochemical interpretation. A biochemical network can be characterized by "minimal metabolic behaviors" and the associated "reversible metabolic space." As shown in [LarBoc09], this method can be implemented computationally.

Graph/Matroid Algebraic Structural Analysis

Further, even within the context of the linearized model there is much more that could be revealed by study of the gross graph and matroid structures within the linearized system matrix, from which the graph and matroid structures within the matrix disclose important controllability properties (see for example [Murota87]). Again, here because of the discrete nature of matroids and graphs, algorithmic tests can be made and extensions provided for examining potential susceptibilities and immunities to variations and disturbances.

Exemplary Architectural Aspects of Comprehensive Computer Tool and its Component Elements As described above, embodiments the invention comprise a computer tool for the study of algebraic structure of signaling networks. These computer tool embodiments can be combined with numerical simulation tools. Such numerical simulations can use incorporations and/or adaptations of existing numerical simulation tools, such as Gepasi (and its extensions and progeny) [Mendes01] and Monod [SGMBE03], but preferably uses a data framework taught later in this patent specification and provide numerical capabilities for accurate simulations of the nonlinear models. Additionally, steady-state equilibrium-condition tools implementing methods such as Elementary Mode Analysis [PSPKSP04], Extreme Pathways [PRPWP03], Flux Balance Analysis [SKBSG02], etc. can be included in various embodiments.

In a modest-scale embodiment, the computer system provides an environment for accurately studying the structural and numerical dynamics of evolving mathematical models for an entire non-trivial human cell.

In larger-scale embodiments, the computer system provides an environment for accurately studying the structural and numerical dynamics of evolving mathematical models for an entire region of human tissue, human organ, or family of interdependent metabolic subsystems.

Figure 8A:
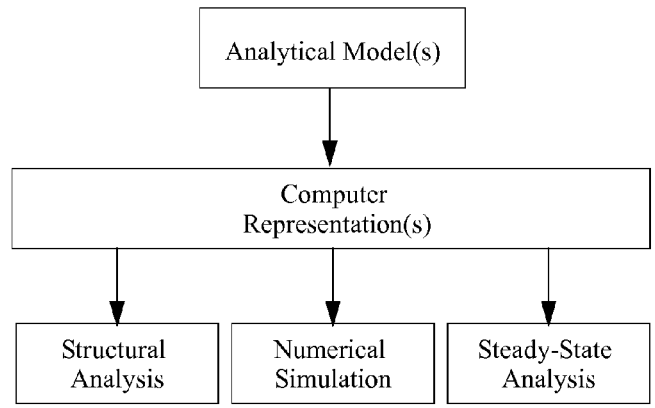
FIG. 8a depicts exemplary arrangements incorporating classes of models as provided for by the invention.

FIG. 8a depicts exemplary arrangements incorporating classes of models as characterized above. Here one or more analytic model(s) are used to create one or more computer representations. These computer representations can be used to drive one or more of structural analysis tools, numerical simulation tools, and/or steady-state equilibrium analysis tools. Ideally, a common computer representation or common collection of computer representations is used to drive each of the structural analysis tools, numerical simulation tools, and/or steady-state equilibrium analysis tools. However, the invention provides for separate or special computer representations to be employed as needed by one or more particular structural analysis tools, numerical simulation tools, and/or steady-state equilibrium analysis tools. In this case the invention further, as would be advantageous, provides for conversion among multiple computer representations so as to limit the number of computer representations that a user may need to oversee and/or hand-enter. The representations can be stored in a problem image (discussed later) and/or other type of data record.

Figure 8B:
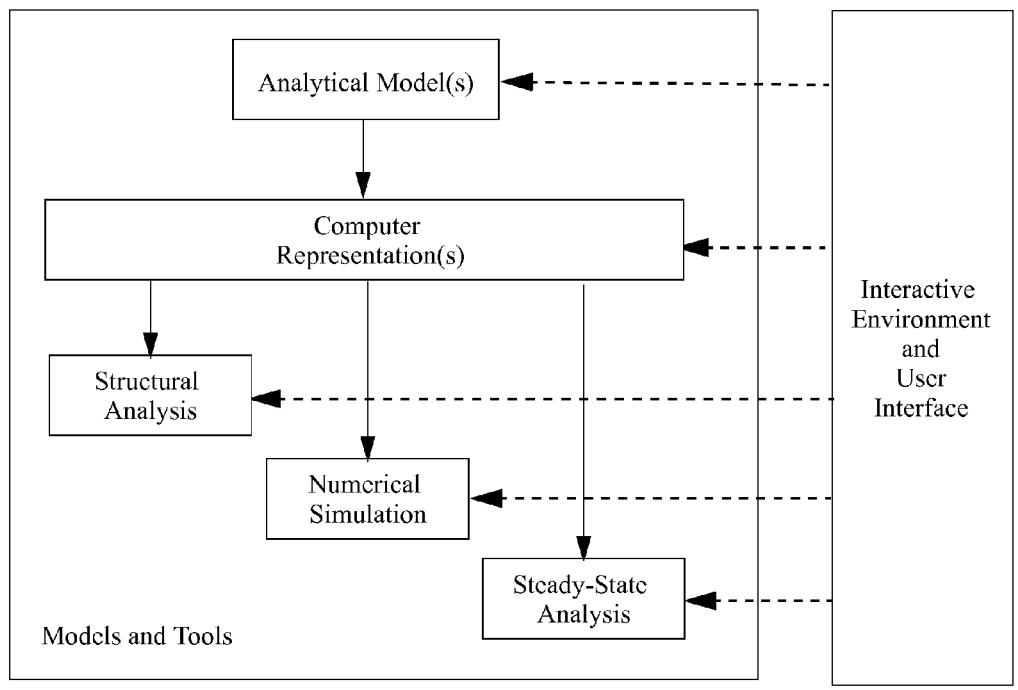
FIG. 8b depicts the arrangement of FIG. 8a is implemented comprising an interactive environment with an associated user interface.

In an embodiment, the arrangement of FIG. 8a is implemented comprising an interactive environment with an associated user interface, as depicted in FIG. 8b.

In an embodiment the invention provides for a modular structure computer system. In various embodiments, the invention comprises one or more of the following functions and capabilities:

A structured catalog of signal transduction pathways, each including:
  A. structural mathematical models of the reaction dynamics;
  B. values of coefficients and parameters of these models;
  C. known related chemistry of the pathway's chemical constituents;

Mathematical tools for studying the structural behavior of these mathematical models, in particular designed to be operative for:
  A. Identification of internal proclivities towards instabilities;

B. Identification of potential sensitivities to known and unknown candidate crosstalk processes;

C. Identification of potential sensitivities to ambient chemical environments;

Utilities to combine isolated models into a larger model which in turn can be checked in the manner above as the combined models (for example, those which crosstalk with one another) as the combined models will likely behave differently than the isolated models;

Utilities to replace models or groups of models with other models or groups of models for various reason, such as but not limited to:

A. Incorporation of improved models;

B. Incorporation of more comprehensive models;

C. Incorporation of simplified models;

D. Incorporation of more isolated models;

E. Incorporation of trial hypothetical models;

F. Incorporation of perturbation(s) and/or control(s) into models;

G. Naturally support evolution of models;

H. Study of legacy models;

A standardized framework, I/O handling, and variable handling for models for various reason, such as but not limited to:

A. Exchange of models among groups of researchers;

B. Provide for sale, licensing, and/or purchase of models.

In an embodiment, an API is provided.

In an embodiment, a module template is provided.

Figure 8C:
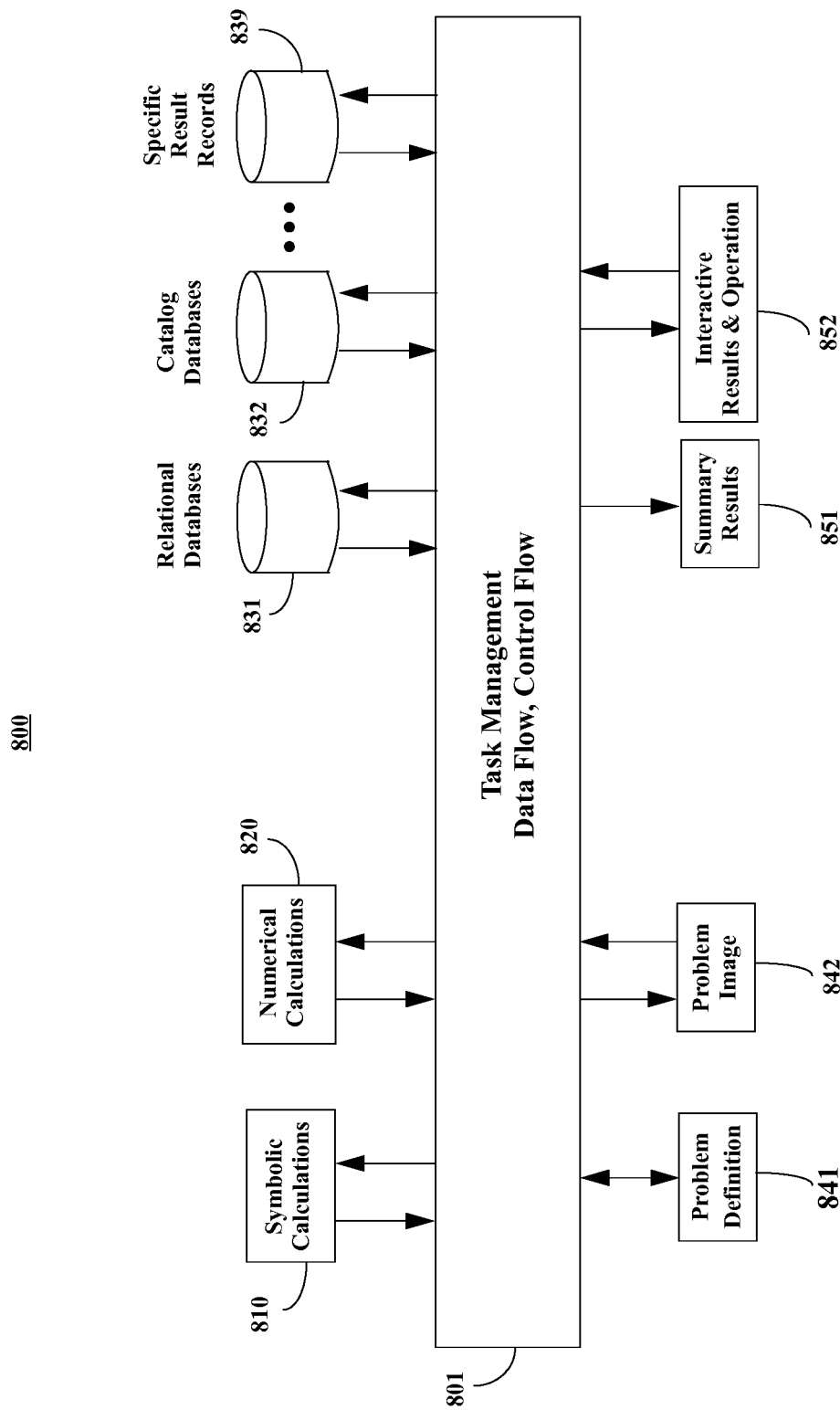
FIG. 8c illustrates an exemplary basic embodiment of a computer tool provided for by the invention.

FIG. 8c illustrates an exemplary architectural overview of an exemplary embodiment 800 of a computer tool as provided for by the invention. In an embodiment, overall task management, data flow and control flow 801 can be combined into a central entity or can be organized to span a group of entities. A problem definition 841, which can include new material, variations on one or more previously entered problem definitions and/or combinations of parts or all of previously entered problem definitions, communicates with the aforementioned task management, data flow and control flow entity/entities. The problem definition can be formulated, submitted, and/or edited using an interactive interface, such as that used to provide interactive results and operation 852, or can be submitted with a separate interactive user interface and/or submitted via other means (email, data record, html form, etc.) The formulated problem definition results in a problem image 842, or can be first submitted to symbolic calculations 810 and/or numerical calculations 820 which result in a problem image 842. The task management, data flow and control flow entity/entities 801 can consult various databases 831, 832 and/or records of previous specific results 839. These can be collocated with the computer tool and/or be located remotely, for example within a research institution, enterprise, or at another location via internet access. Models and analysis are performed by employing symbolic calculations 810 and/or numerical calculations 820 which produce results. These results can be summarized 851 and presented to the user or other audience, and/or or presented interactively 852. The results can additionally or alternatively be stored in a repository 839 for future access. Results stored in the repository 839 can be called up for review 851 or presented interactively 852.

Figure 9:
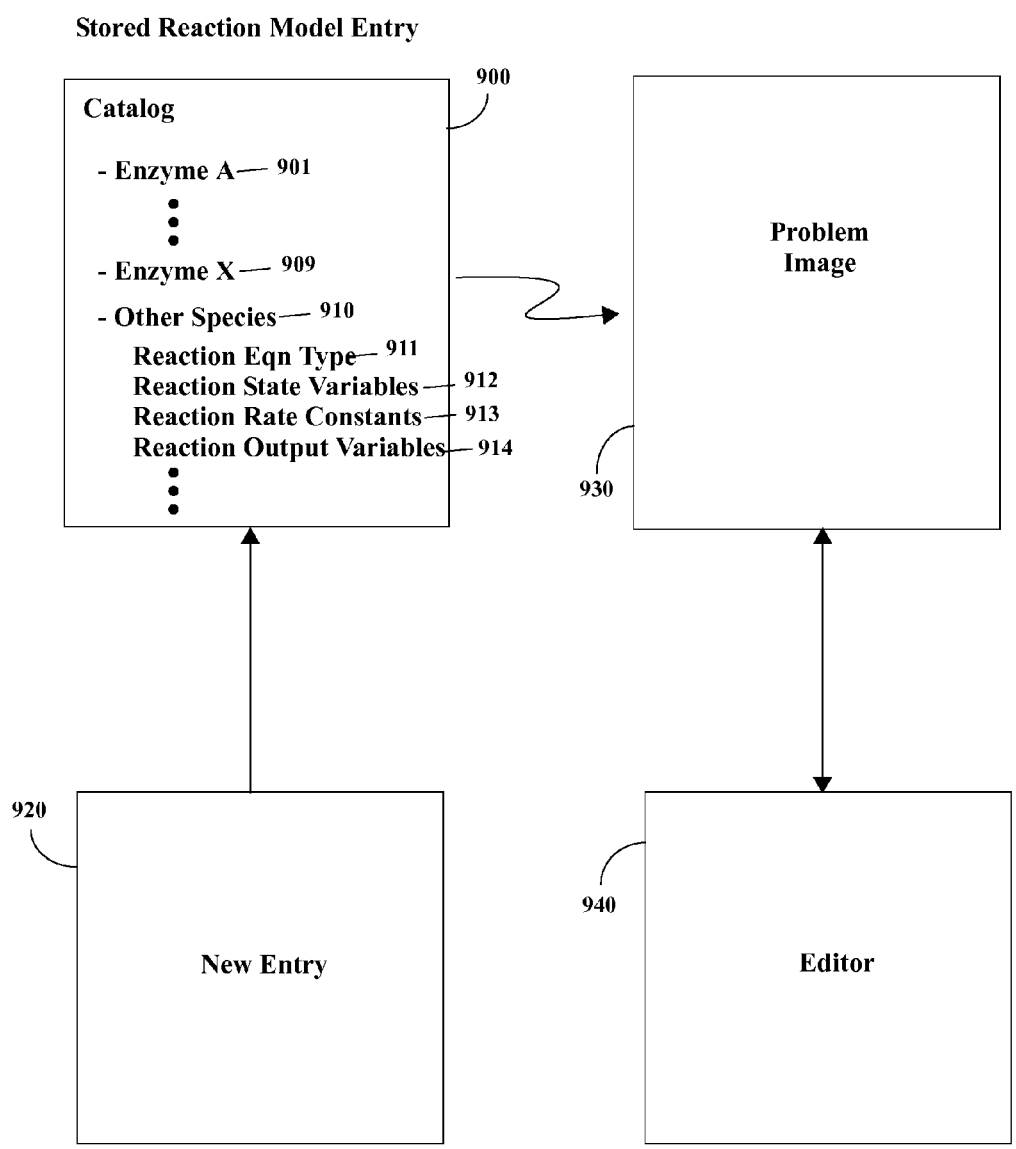
FIG. 9 illustrates exemplary data arrangements and transactions among stored reaction model entries, the active problem image, new entries, and an editor.

In an embodiment, the invention provides for entering and editing of reactions and cascades of reactions. FIG. 9 illustrates exemplary data arrangements and transactions among stored reaction model entries, the active problem image, new entries, and an editor. For example, a new entry 920 can be created using a user interface or other means and submitted to a catalog in the system where it serves as a record 900 that can be referred to in future use for many potential problems, analyses, simulations, and other applications. As an illustrative (but not limiting) example, specific enzymes in an enzyme or signaling cascade can be listed 901, 909. In an embodiment, these enzymes can be referenced to other models and records already entered into the system. Additionally other species 910, such as ions, ligands, cytokines, growth factors, hormones, etc., can be entered, along with various aspects and/or parameters of the individual reaction(s) (for example but not limited to 911-914). These records can be incorporated into a problem image 930. In an embodiment, the problem image can be created and/or modified by an editor 930.

Transformations Among Pathways and Datasets

In an embodiment, the invention provides utilities for adapting data and properties of one signaling pathway for use as is or in a modified form of the pathway. Examples include split, merge, and substitute. The invention provides for any one or more of source, target, and resultant signaling pathways to comprise feedback, feedforward, allosteric and/or non-allosteric modulation attributes and components.

Figure 10A:
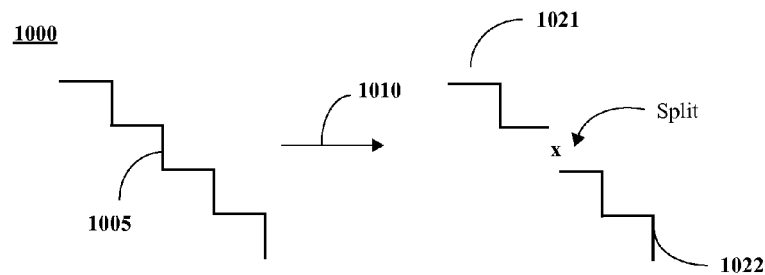
FIG. 10a illustrates an exemplary split operation on an exemplary signaling transduction cascade.

In an embodiment, the invention provides utilities for split/break operations to break a signaling cascade into two or more fragments. FIG. 10a illustrates an exemplary split/break operation 1010 at a specific location 1005 on an exemplary signaling cascade 1000. The split/break operation can be implemented at a node or in a step in the pathway. The result is at least two fragments (here 1021, 1022) of the original pathway 1000 which can be used as components for an immediate problem or study, and/or can be retained in a system catalog for future use.

Figure 10B:
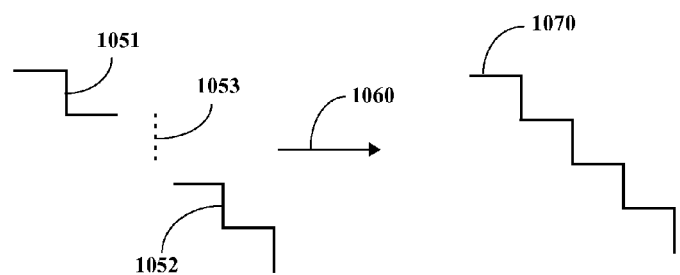
FIG. 10b illustrates an exemplary merge/splice/join operation an exemplary signaling cascade.

In an embodiment, the invention provides utilities for splice/merge/join operations to merge two or more fragments into a resultant merged signaling cascade. In an embodiment, such splice/merge/join operations can be implemented at a node or step in the pathway. In an embodiment, such splice/merge/join operations can introduce a new node or pathway hop in a step in the pathway. FIG. 10b illustrates an exemplary splice operation a pair of exemplary signaling pathways and/or fragments of signaling pathways. In this example, two signaling pathways or fragments of signaling pathways, or one of each—these represented as 1051 and 1052—are joined, in this case via an introduced pathway 1053, by a splice operation 1060 to produce a new pathway 1070.

Figure 10C:
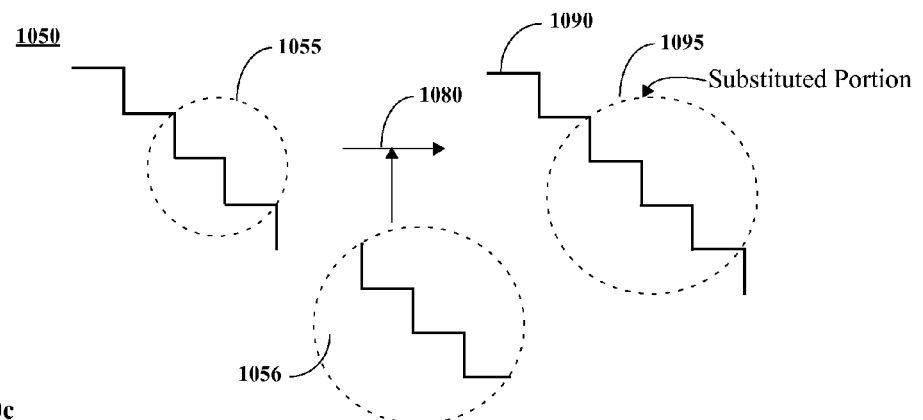
FIG. 10c depicts an exemplary substitution operation an exemplary signaling cascade.

In an embodiment, the invention provides utilities for substitution operations on signaling cascade wherein a specific portion of a signaling cascade is identified and replaced with an alternate topologically-compatible portion of a signaling cascade. FIG. 10c depicts an exemplary substitution operation 1080 wherein a specific portion 1055 of a signaling cascade 1050 is identified and replaced with an alternate topologically-compatible segment of a signaling cascade 1056 to produce a resulting signaling cascade 1090 comprising the substituted segment 1056 in place of the selected portion 1055. Note, as depicted in the Figure, the substituted segment 1056 can be of a different length than that of the selected portion 1055. Additionally, as mentioned earlier and although not depicted, either or both of the substituted segment 1056 and/or the selected portion 1055 can comprise feedback, feedforward, allosteric and/or non-allosteric modulation attributes and components.

Figure 11A:
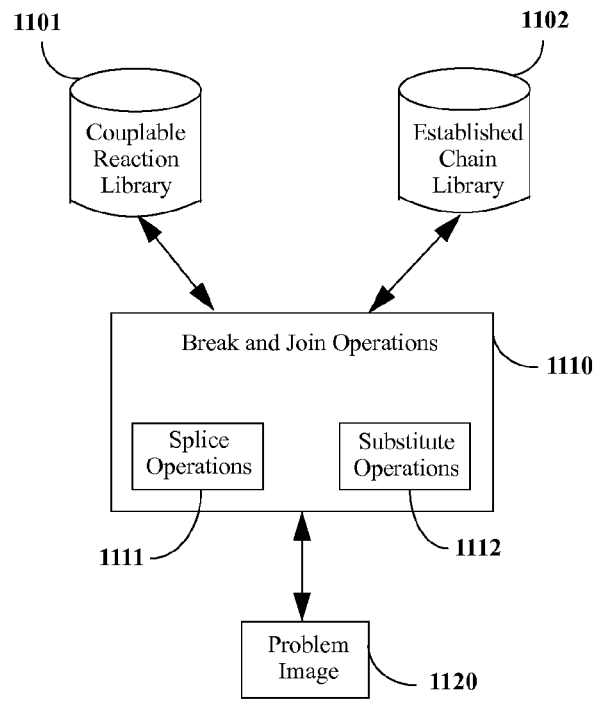
FIGS. 11a and 11b depict an exemplary environment for applying the operations of FIGS. 10a-10c to a signaling cascade as provided for by the invention.
Figure 11B:
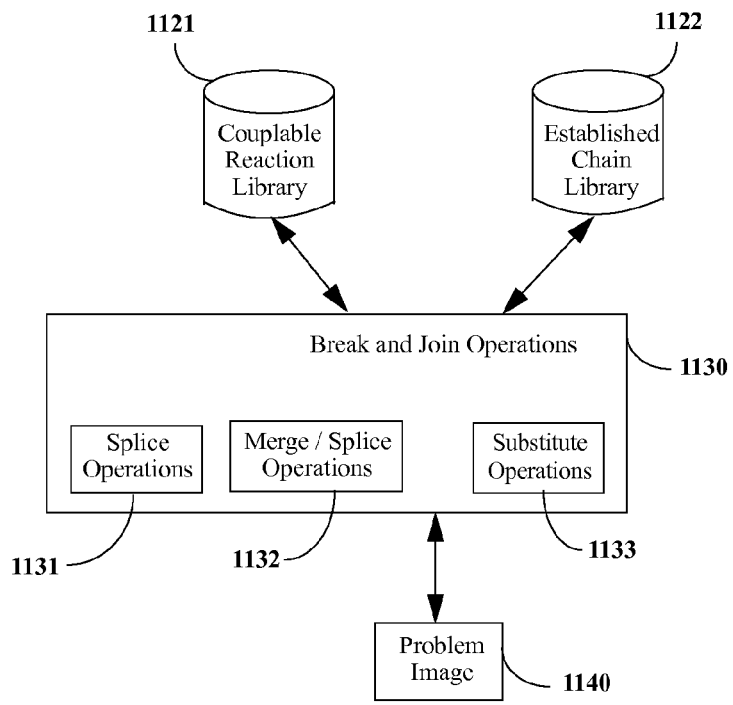

In an embodiment, the invention provides an environment for transformational operations on signaling cascades. FIG. 11a illustrates an exemplary environment 1110 for implementing transformational operations from FIGS. 10a-10c to a signaling cascade as provided for by the invention. In an embodiment, only some 1111, 1112 of the transformational operations taught above are provided (for example, split/ break operations are not included). In an embodiment, the environment 1110 can interact with other aspects and elements of the computer tool, for example one or more of a problem image 1120, an established chain library 1102, and/ or a couplable reaction library 1101. FIG. 11*b* illustrates another exemplary 1130 environment wherein all transformational operations 1131, 1132, 1133 from FIGS. 10*a*-10*c* are implemented.

Exemplary Disturbance Study Utilities and Modules

Figure 12A:
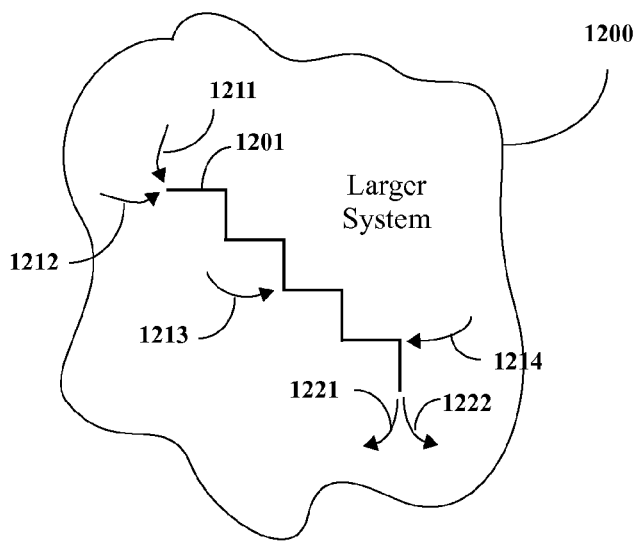
FIG. 12a illustrates an exemplary signal transduction cascade in a larger chemical system.
Figure 12B:
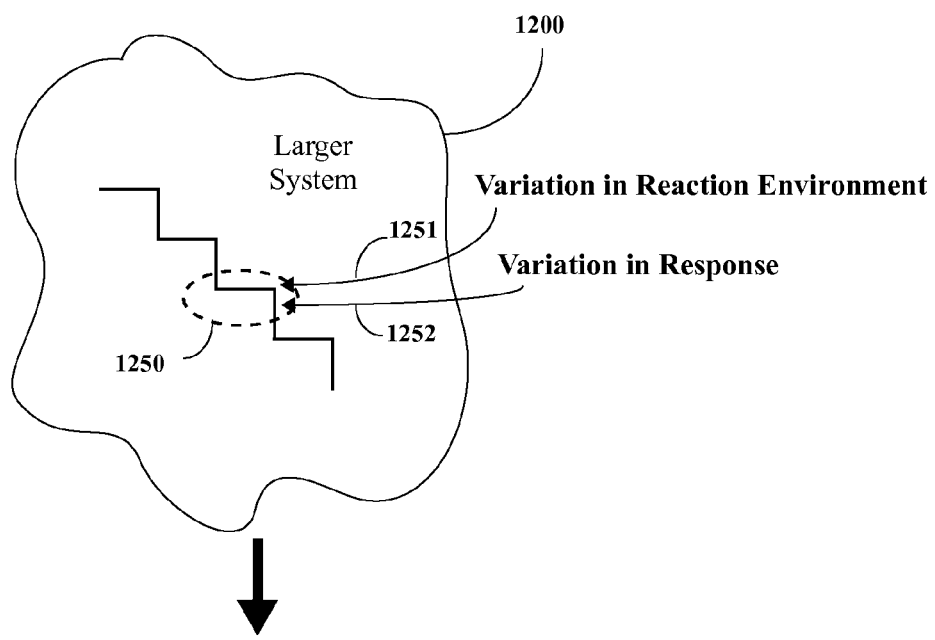
FIG. 12b illustrates exemplary disturbances directed towards the exemplary signal transduction cascade of FIG. 12b.

In an embodiment, the invention provides utilities for introducing variations in one or more of:

- the local reaction environment for one or more steps of a signaling cascade;
- the global reaction environment for an entire signaling cascade;
- the global reaction environment for a group of signaling cascades;
- the response of one or more steps in one or more steps of a signaling cascade;
- the response in environment of one or more steps in a group of signaling cascades as well as other variations. For example, FIG. 12*a* illustrates an exemplary signal transduction cascade in a larger system 1200. Variations 1211, 1212 can be introduced at the beginning of the cascade, and/or variations 1221, 1222 can be introduced at the end of the cascade. Additionally, variations 1213, 1214 can be introduced at selected nodes of the cascade. Further, where meaningful biochemically, variations 1201 can be introduced in the pathway of the cascade. As an example, FIG. 12*b* illustrates exemplary reaction environment 1251 disturbances and variations in response 1252 directed towards a portion 1230 of the exemplary signal transduction cascade of FIG. 12*a*.

Figure 13:
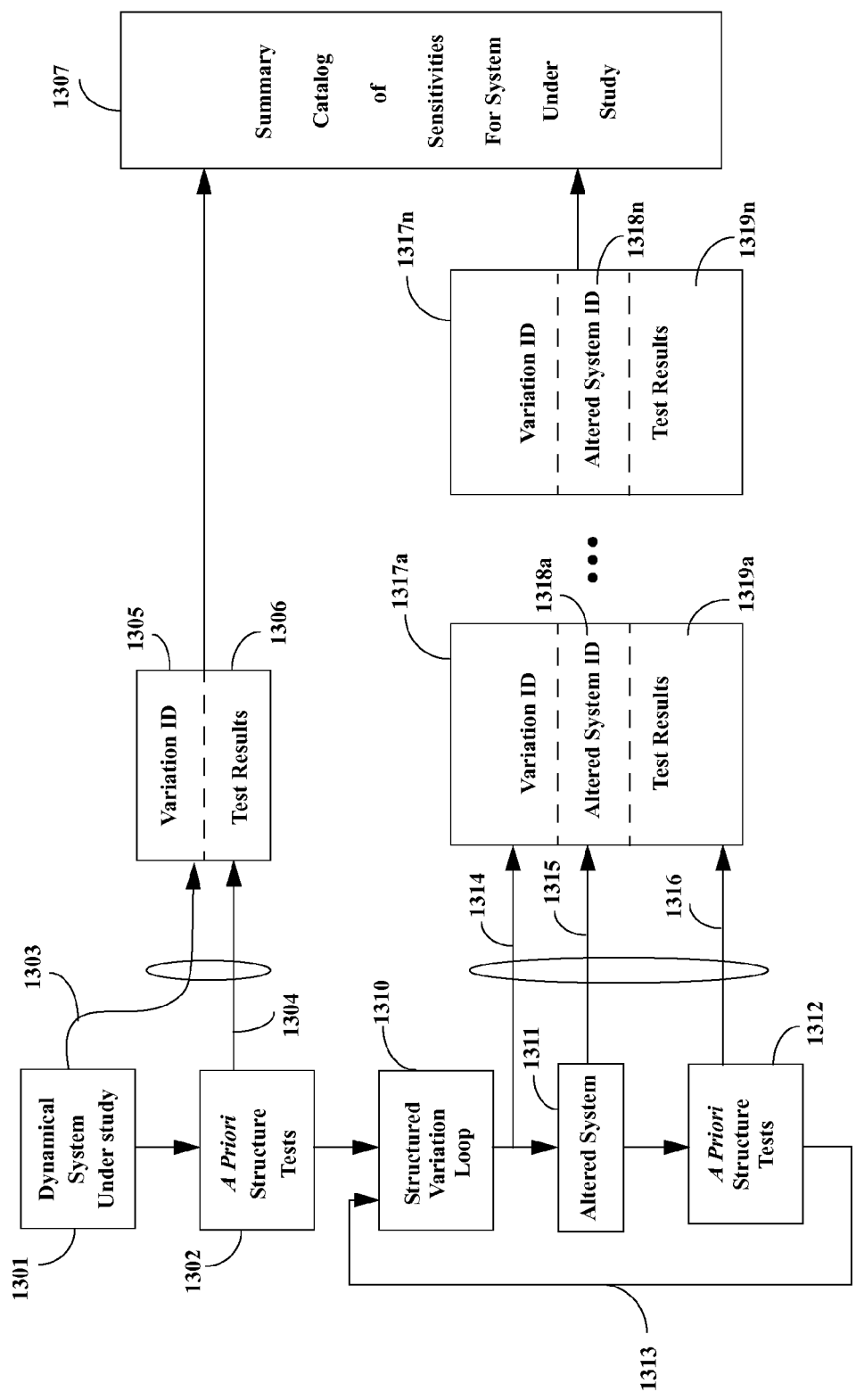
FIG. 13 illustrates an exemplary variational study environment embodiment for the study of disturbances that can be included in the computer tool provided for by the invention.

In an embodiment, the invention provides an environment for variational operations and study on signaling cascades. FIG. 13 illustrates an exemplary variational study procedure made possible by an exemplary environment for the study of disturbances and responses. These can be included in the computer tool provided for by the invention, although many other variations are possible and are anticipated for use in other embodiments of the invention. In this example, a system of signaling pathways 1301 are subjected to a priori tests 1302 producing outcomes 1304 that are paired with an identifier 1303 for the system to create a record comprising an ID 1305 and test results 1306 that can be provided to a catalog 1307 for future comparative use. A series of variational tests (for example, as can be used to generate a plot) are implemented via an iterative loop 1310 that creates a sequence of altered systems 1311 that are in turn subjected to a series of a priori tests 1312. In an embodiment, the tests 1312 may vary according to test results or test parameter values. In an embodiment, the results 1313 of these tests 1312 can be directed to the iterative loop 1310 so as to control the operation of the iterative loop 1310. The series of tests produce Ids 1314 and/or 1315 and results 1316 that form a series of n records, each record respectively comprising elements 1317*a*, 1318*a*, 1319*a* through elements 1317*n*, 1318*n*, 1319*n* for some integer n. These records can be provided to a catalog 1307 for future comparative use.

Figure 14:
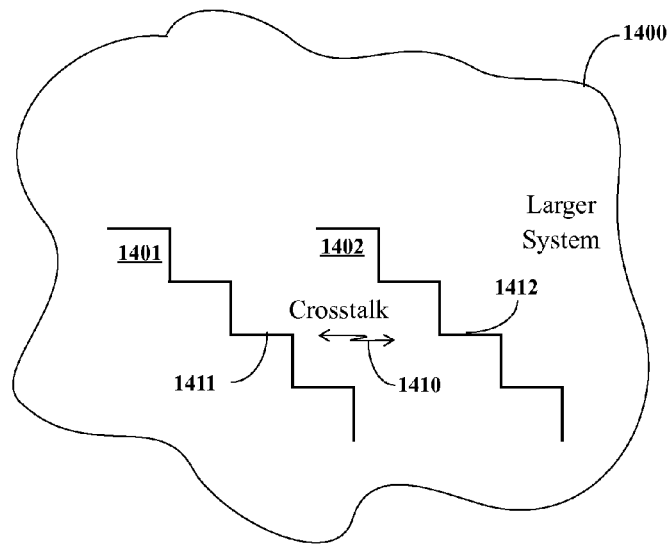
FIG. 14 illustrates exemplary crosstalk among exemplary signal transduction cascades in a larger chemical system.
Figure 15:
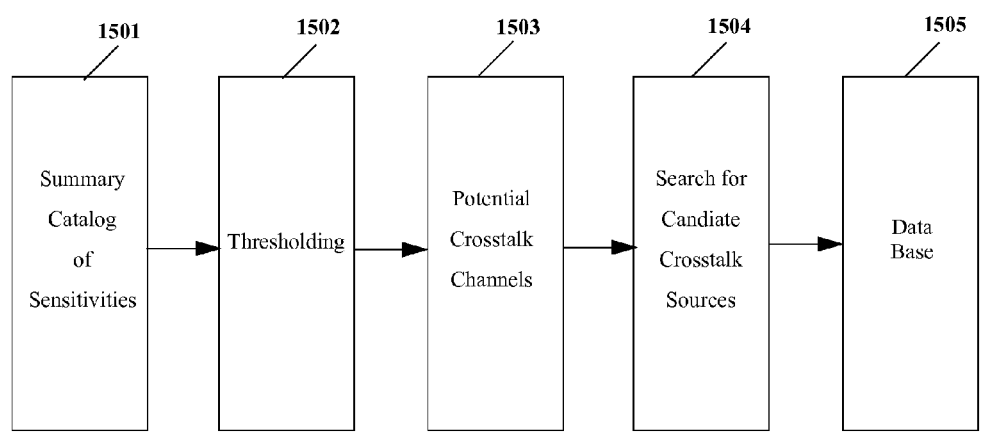
FIG. 15 illustrates an exemplary crosstalk study environment embodiment that can be included in the computer tool provided for by the invention.

In an embodiment, the invention provides an environment for the introduction and study of crosstalk among signaling cascades. FIG. 14 illustrates exemplary crosstalk operation or linkage 1410 among particular pathway segments 1411, 1412 comprised by an exemplary pair of signaling cascades 1401, 1402 in a larger system of signaling cascades 1400. The invention provides for crosstalk to occur at nodes instead of or along with crosstalk in signaling paths. The invention also provides for the crosstalk model to permit an adjustable degree of coupling. FIG. 15 illustrates an exemplary crosstalk study environment embodiment for potential crosstalk identification that can be included in the computer tool provided for by the invention. In this example, a catalog 1501 of sensitivities relevant to crosstalk studies can be determined by various means, including algebraic structural analysis, known information, hypothesis, etc. If useful, thresholding operations 1502 can be used to bring in or withdraw individual crosstalk candidates based on the degree of coupling under study. From this, operations 1503 can be performed to determine potential channels in which crosstalk reception can occur. From this, operations 1504 can be performed to determine potential crosstalk sources; these include not only chemical matching but, as may be desired, localization controls, diffusion models, etc. In an embodiment, the final results of the preceding steps can be stored in a database.

Exemplary State-Variable Cross-Product Dynamics Study Modules

Figure 16:
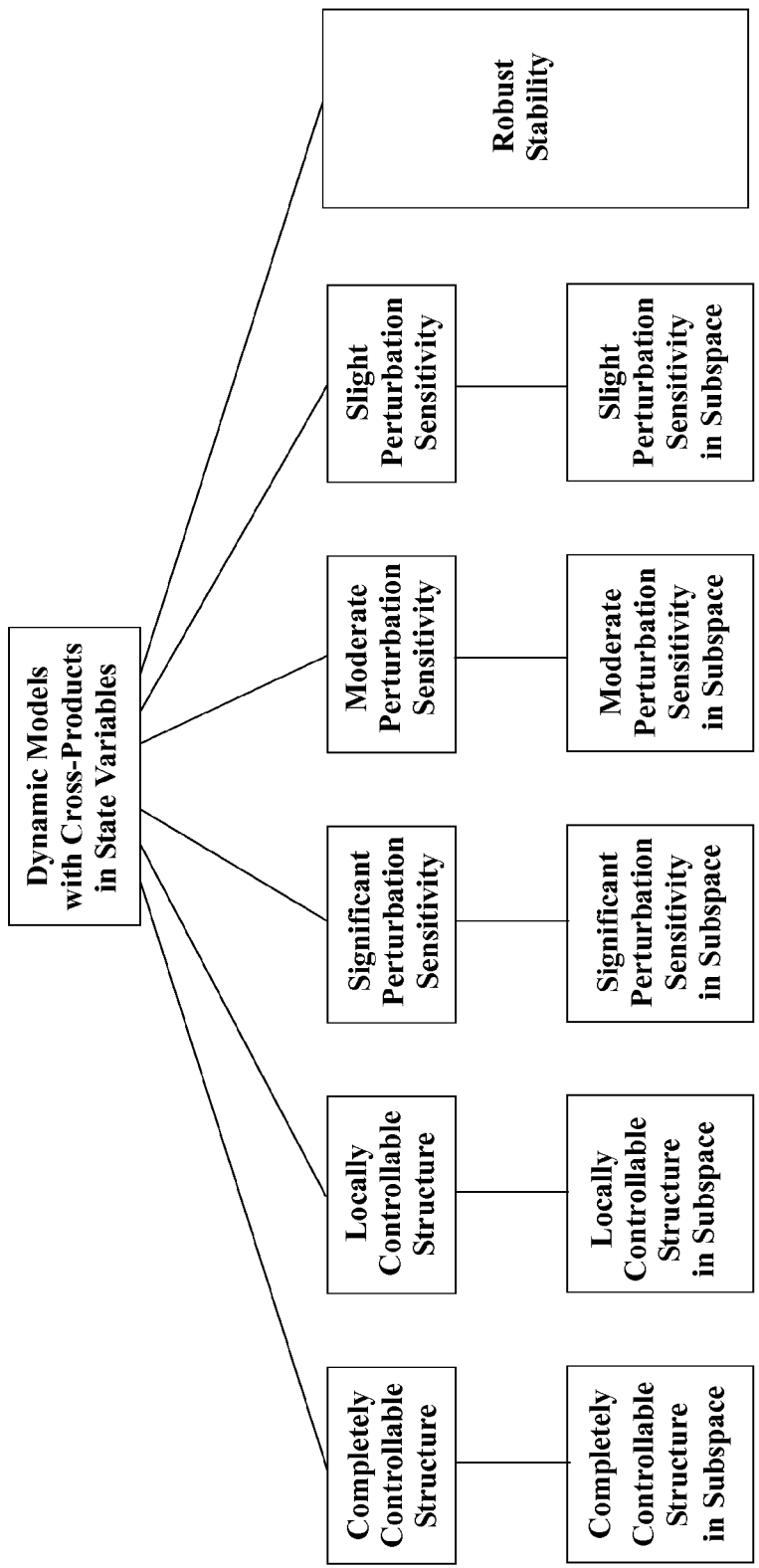
FIG. 16 illustrates an exemplary classification taxonomy of system dynamics comprising cross-products among state-variables.
Figure 17A:
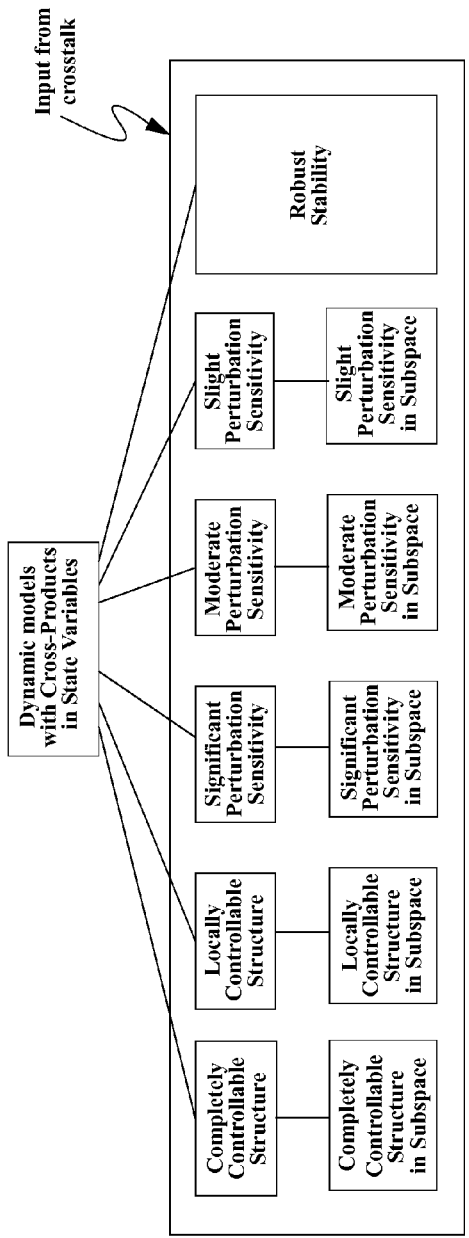
FIG. 17a illustrates the embedding of the exemplary classification taxonomy of FIG. 16 into an exemplary study environment pertaining to exogenous input cross-talk as provided for by the invention.
Figure 17B:
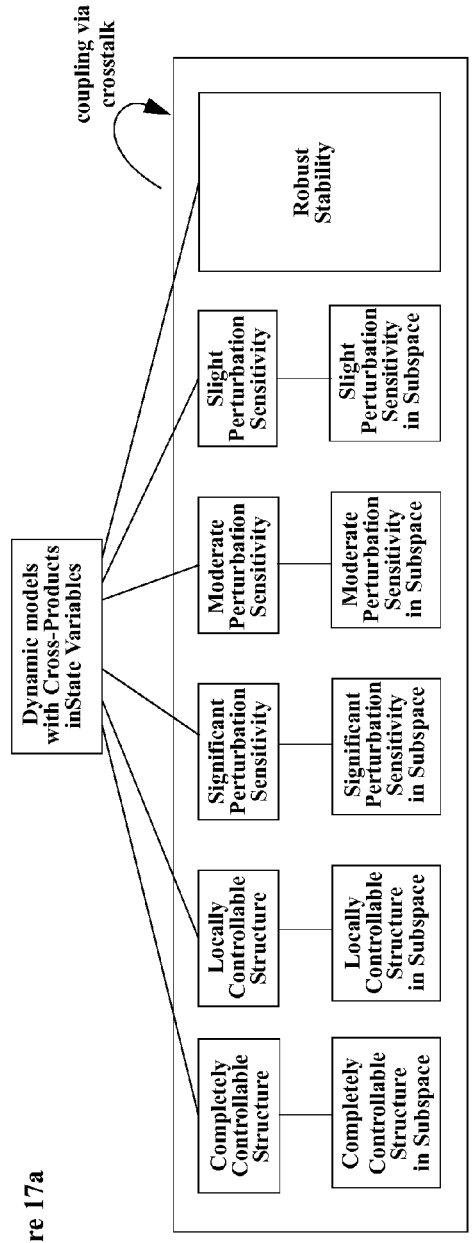
FIG. 17b illustrates the embedding of the exemplary classification taxonomy of FIG. 16 into an exemplary study environment pertaining to internal cross-talk as provided for by the invention.

FIG. 16 illustrates an exemplary classification taxonomy of system dynamics which comprise cross-products among state-variables. Other arrangements similar in spirit and scope are also possible and are provided for by the invention. The invention provides for such a taxonomy, or a similar taxonomy, to be used for additional study of other aspects of the invention. For example, FIG. 17*a* illustrates an exemplary embedding of the exemplary classification taxonomy of FIG. 16 into an exemplary cross-talk-input study environment as provided for by the invention. As another example, FIG. 17*b* illustrates the embedding of the exemplary classification taxonomy of FIG. 16 into an exemplary study environment pertaining to coupled cross-talk as provided for by the invention.

Figure 18:
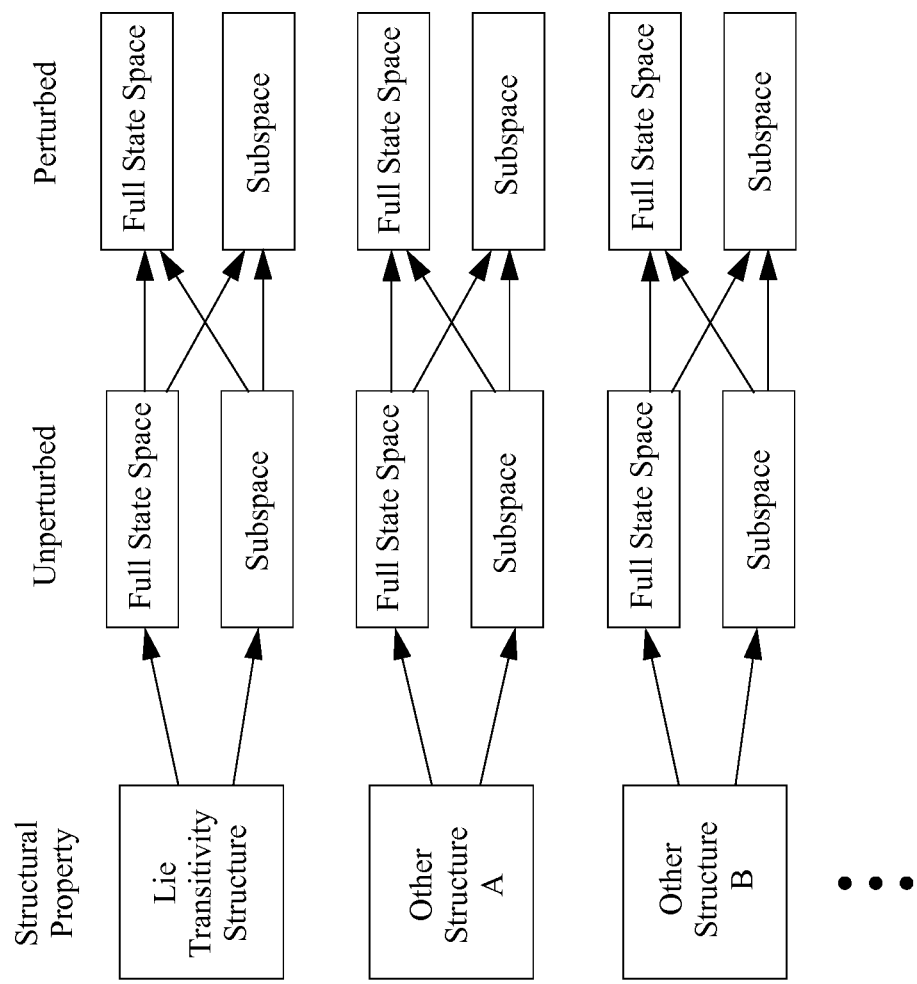
FIG. 18 illustrates computer analysis tools for the structural study of unperturbed and perturbed versions of a state-space dynamical system model that can be included in the computer tool provided for by the invention.

FIG. 18 illustrates an exemplary organization that can be used by the computer analysis tools for the structural study of unperturbed and perturbed versions of one or more state-space dynamical system models that can be included in the computer tool provided for by the invention. The depicted exemplary study environment permits study of the full state space or partial subspaces leveraging the subspace results from [Ludwig80], subgraph properties, flux cone partitions, etc. as may be advantageous in applications.

The invention provides for modules that link models and data with bilinear system representation matrices. Transformations can be made among biochemical model representations, data, and bilinear system representations.

The invention provides for Lie algebra calculations are described above and in [Ludwig 80]. As described above, transitivity tests over pairs of control cross product matrices with respect to the Lie bracket operation [Ludwig 80], [Kucera67], [Boothb75] can be readily iterated through sequences of Lie bracket operations and rank tests can be performed to establish controllability with respect to disturbances in substrates or from crosstalk. As shown in [Ludwig 80], this can be done for subspaces of the dynamics as well as the full dynamics of the system.

Sensitivity tests can be automated to test to see if small perturbations in the model matrices result in the controllability. Threshold tests can be used to determine rank ranges. These can leverage precomputed catalogs, for example using the methods of [Boothb75], of controllable matrix sets.

In various embodiments, the invention can include one of more of the following elements:

In an embodiment the computer tool interfaces with established enzyme and signaling databases that can be made locally available.

In an embodiment the computer tool interfaces with established enzyme and signaling databases available over the internet.

In an embodiment the computer tool interfaces provides a modular framework for computer representations of models so that a variety of models can be exchanged, upgraded, substituted, modified, etc.

In an embodiment the computer tool comprises one or more hysteresis modeling and/or analysis modules that can be used to characterize or emulate hysteric processes, for example as can occur in allosteric enzymes due to conformational changes.

In an embodiment the computer tool comprises interactions among numerical dynamics and symbolic calculation elements.

In an embodiment the computer tool comprises pathway structure visualization modules.

In an embodiment the computer tool comprises pathway crosstalk visualization modules.

In an embodiment the computer tool comprises pathway dynamics visualization modules.

The invention provides for the handling of more general chemical reaction networks. This can include use as a tool for the design, operation, and failure analysis of sequential chemical reactions.

Transformation Transactions and an Associated Comparison Tests

Figure 19:
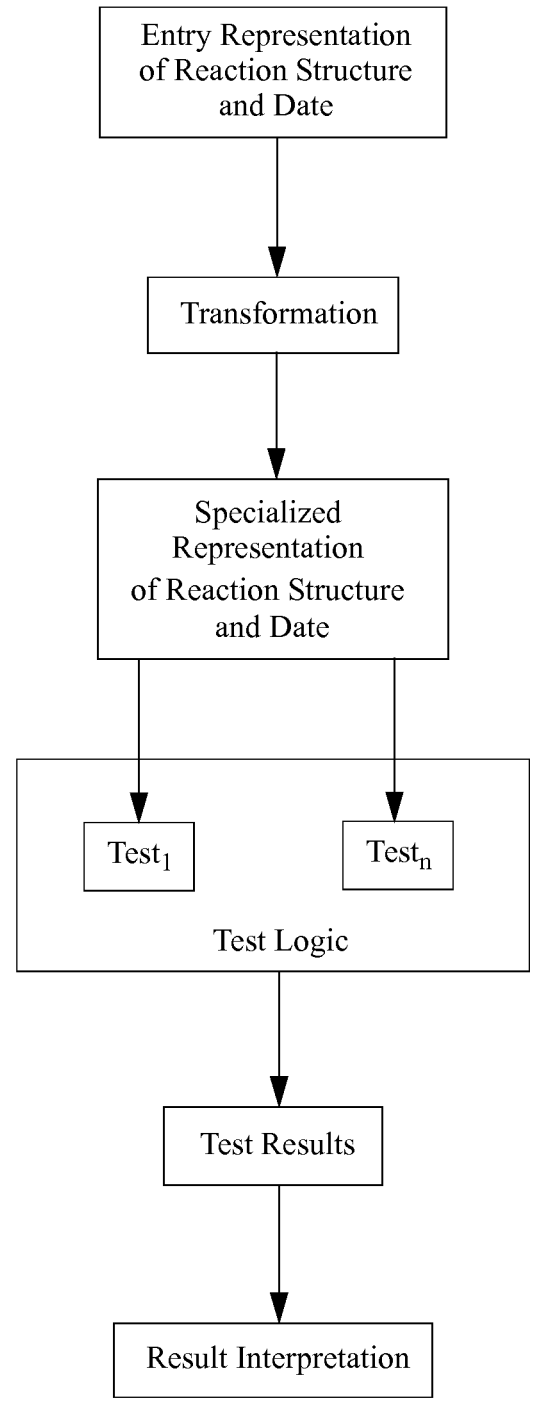
FIG. 19 shows an exemplary transformation transaction with an associated comparison test as provided for by the invention.

The invention provides for the computer tool to comprise utilities for transformation transactions and an associated comparison tests. For example, FIG. 19 depicts an exemplary transformation transaction and an associated comparison test as provided for by the invention. Other variations are possible and are also provided for by the invention.

Application of the Invention to Open Metabolic Research Problems

Figure 20:
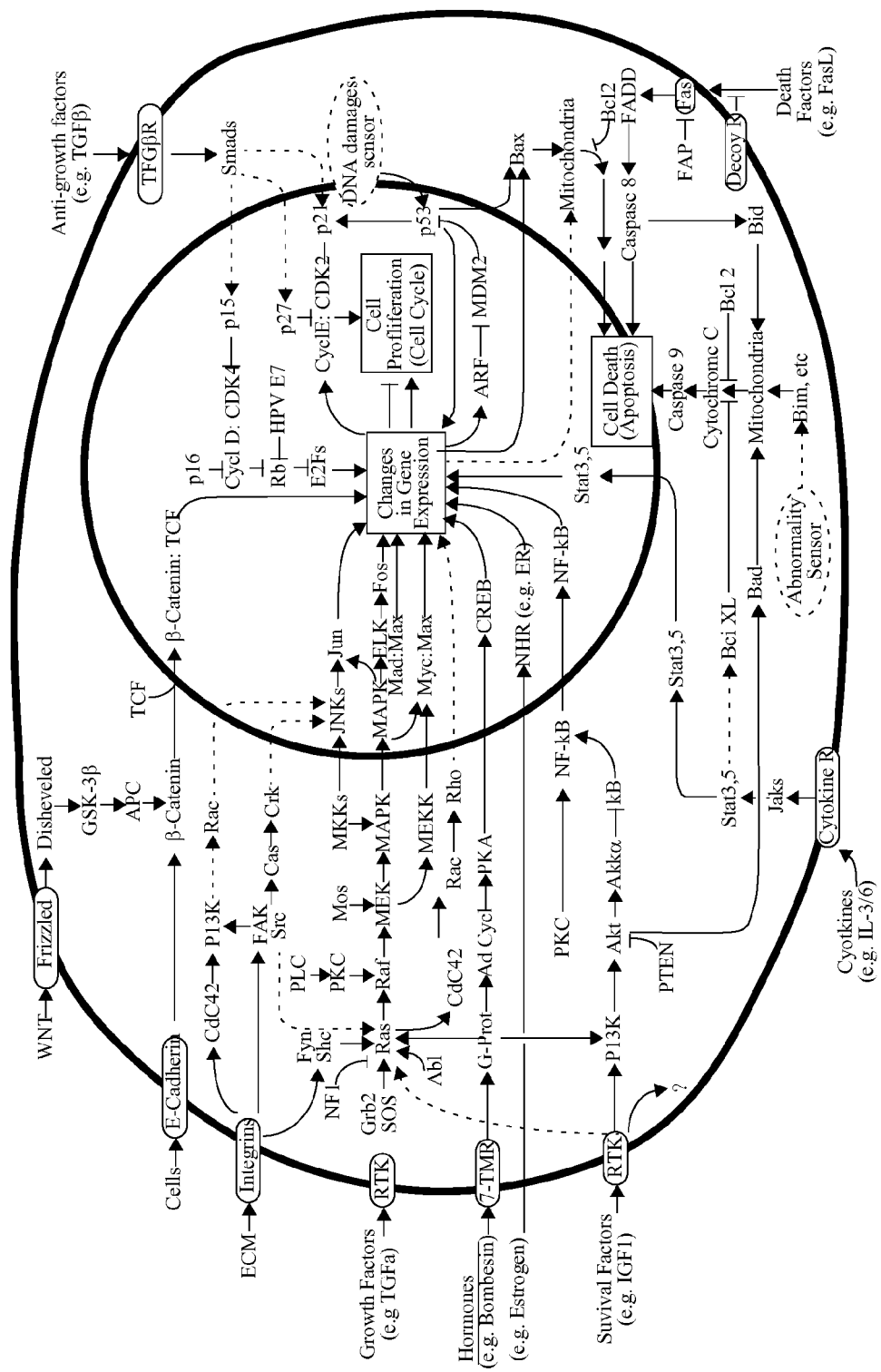
FIG. 20 (adapted from [Potapo08]) shows a simplified exemplary rendering of a the major pathways in an archetypical mammalian cell

The complexity of signaling networks is just beginning to be appreciated and somewhat cataloged, characterized and understood. Vast amounts of findings and hypothesis are being published monthly worldwide. FIG. 20 (adapted from [Potapo08]) shows a simplified exemplary rendering of a the major pathways in an archetypical mammalian cell, but this is hardly representative. Almost every pathway depicted is known to have extensive additional structure, with new pathways, crosstalk, enzyme properties being discovered all the time. With this by the way of orienting background, together with many aspects of the invention and the significant complexity which it can handle and explore as knowledge evolves, the invention is seen to offer tremendous potential value.

The present invention could be expected to provide value in the following open areas of study:

The wide range of noteworthy nonlinear behavior, including periodic behavior, hysteresis, chaos, self-organization, and forbidden states.

Potential susceptibilities to potential instabilities from small disturbances or variation arising from higher-order algebraic structural properties.

Aspects arising specifically from the cross-product of state variables which remain to be studied in earnest.

Aspects relating to structural controllability which could be studied further

At least some of these higher-order algebraic structural properties can be determined by algorithmic tests, suggesting a new bioinfomatics application area Creation of tests for the higher order algebraic structures and a general mathematical perturbation/sensitivity analysis could reveal potential susceptibilities to crosstalk or shifts in the ambient chemical environment.

Can a generalized approach for bioinfomatic "reaction-structural calculators" be synthesized?

Are there yet other types of exploitable matrix algebra structures, such as the cousin to Lie matrix algebras of Jordan matrix algebras?
  Lie bracket operation provides antisymmetric part of a matrix product
  Jordan bracket operation provides symmetric part of a matrix product The Lie algebra aspects turn out to involve an imbedded interaction of two linearly independent vector fields.
  Could there be higher-order imbedded interactions that involve more than two linearly independent vector fields?

As bilinear systems exhibit types of hysteretic effects:
  Could unknown hysteretic effects be hidden within certain metabolic enzyme cascade dynamics?
  Could inclusion of further bilinear terms be useful in modeling know hysteretic behavior of some enzymes thought to arise from conformational transitions; see e.g. [Kurgan95]?

As the cross-products in state variables can be associated with mathematical structures called quadratic forms, could further hidden aspects of metabolic enzyme cascades be explored using vector generalizations of quadratic forms rather than bilinear system representations?

Assemble a catalog of system-of-equations representations for a range of important exemplary signaling transduction networks and metabolic enzyme/kinase cascades, with a particular emphasis on the limit understanding of those with the relatively unstudied bilinear system mathematical structure;

Assemble an overlapping catalog of families of exemplary signaling transduction networks and metabolic enzyme/kinase cascades with known cross-talk paths;

Characterize structural and variation sensitivities of abstract bilinear systems that have Lie algebraic transitivity substructures (which can thus be driven into instability);

Examine the relationship between these mathematical proclivities towards instability and the know behavior of cataloged signaling transduction networks and metabolic enzyme/kinase cascades;

Attempt to identify candidate crosstalk areas that could lead to Lie structure instability so as to help pinpoint future biochemical searches for previously unknown crosstalk processes;

Attempt to identify candidate variational areas that could lead to Lie structure instability so as to help pinpoint future biochemical searches for previously unknown changes influencing network/cascade dynamics;

Attempt to formulate explicit testing techniques for studying these properties of signaling transduction networks and metabolic enzyme/kinase cascades which will be identified and characterized in the future.

While the invention has been described in detail with reference to disclosed embodiments, various modifications within the scope of the invention will be apparent to those of ordinary skill in this technological field. It is to be appreciated that features described with respect to one embodiment typically may be applied to other embodiments. Therefore, the invention properly is to be construed with reference to the claims.

REFERENCES

[AgaGaj95] Z. Aganovic and Z. Gajic, *Linear Optimal Control of Bilinear Systems—With Applications to Singular Perturbations and Weak Coupling*, Springer-Verlag, Piscataway, April 1995.

[AliSar97] M. Alison and C. Sarraf, *Understanding Cancer—From Basic Science to Clinical Practice*, Cambridge University Press, New York, 1997.

[BaMiZi75] H. T. Banks, R. P. Miech and D. J. Zinberg, "Nonlinear Systems in Models for Enzyme Cascades," from *Variable Structure Systems with Application to Economics and Biology, Lecture Notes in Economics and Mathematical Systems*, vol. 111, pp. 265-277, Springer-Verlag, New York, 1975.

[Breire07] S. Beirer, *Mathematical Modelling of the Jak/Stat1 Signal Transduction Pathway*, Logos Verlag Berlin, 2007.

[BinHei02] B. Binder and R. Heinrich, "Dynamic Stability of Signal Transduction Networks Depending on Downstream and Upstream Specificity of Protein Kinases," pp. 1-5, Kluwer Academic Publishers, 2002.

[Bluthg01] N. Bluthgen, H. Herzel, "MAP-Kinase-Cascade: Switch, Amplifier, or Feedback Controller?" $2^{nd}$ Workshop on Computation of Biochemical Pathways and Genetic Networks, Berlin, Logos-Verlag, 2001, pp. 55-62.

[Bluthg02] N. Bluthgen, *Dynamical Models of Signal Transduction and the Influence of Feedback Loops*, TU-Berlin Thesis in Physics, June 2002.

[Boyd91] A. Boyd, *Intracellular Signaling Mechanisms and the Pathophysiology of Disease (Current concepts)*, Boyd, A., Upjohn Company, 1991.

[Bose82] N. K. Bose, *Applied Multidimensional Systems Theory*, Van Nostrand Reinhold Company, New York, 1982.

[Boothb75] W. M. Boothby, "A Transitivity Problem From Control Theory," from *Journal Differential Equations*, vol. 17, pp. 296-307, 1975.

[BrCaMZ04] H. Bradlow, L. Castagnetta, L. Massimo, K. Zaenker, *Signal Transduction and Communication in Cancer Cells*, New York Academy of Sciences, 2004.

[BrGaGe77] C. Bruni, A. Gandolfi and A. Germani, "A Bounded Rate Model for Mass Action Multiple Binding Processes: Stability Analysis," from *Recent Developments in Variable Structure Systems, Economics and Biology (Lecture Notes in Economics and Mathematical Systems)*, pp. 44-67, Springer-Verlag, New York, 1977.

[BrGiKS75] C. Bruni, M. Giovenco, G. Koch and R. Strom, "The Immune Response as a Variable Structure System," in Lecture Notes in Economics and Mathematical Systems: Variable Structure Systems with Application to Economics and Biology, A. Ruberti and R. Mohler (Eds.), pp. 244-264, Springer-Verlag, Berlin, 1975.

[Brocke75] R. W. Brockett, "On the Reachable Set for Bilinear Systems," from *Variable Structure Systems with Application to Economics and Biology, Lecture Notes in Economics and Mathematical Systems*, vol. 3, pp. 54-63, Springer Verlag, Berlin, 1975.

[BucBuc68] M. Buc and H. Buc, "Allosteric Interactions between AMP and Orthphosphate Sites on Phosphorylase b from Rabbit Muscle," in E. Kvamme, A Pihl, ed., *Regulation of Enzyme Activity and Allosteric Interactions (Proceedings of the Fourth Meeting of the Federation of European Biochemical Societies*, Oslo, 1967) Academic Press, New York, p. 111.

[CarBri07] E. Carafoli, M. Brini, *Calcium Signalling and Disease: Molecular Pathology of Calcium (Subcellular Biochemistry)*, Springer, 2007.

[Chow39] W. L. Chow, "Uber Systeme Von Linearen Partiellen Differential-Gleichungen Erster Ordinung," *Mathematics Ann.*, Vol. 117, pp. 98-105, 1939.

[Frank03] D. A. Frank, *Signal Transduction in Cancer*, Kluwer, 2003.

[HeNeRa02] R. Heinrich, B. G. Neel, T. A. Rapoport, "Mathematical Models of Protein Kinase Signal Transduction," *Molecular Cell*, Vol. 9, 2002, pp. 957-970.

[Kincai93] R. Kincaid, "Calmodulin-Dependent Protein Phosphatases from Microorganisms to Man," in *The Biology and Medicine of Signal Transduction (Advances in Second Messenger and Phosphoprotein Research)* (Vol 27), S. Shenolikar, A. Nairn ed., Raven Press, 1993.

[KocHei08] I. Koch, M. Heiner, "Petri Nets," in B. Junker, F. Schreiber, ed. *Analysis of Biological Networks*, John Wiley & Sons, Inc., Hoboken, 2008.

[KraBre63] N. N. Krasovskii and J. L. Brenner, *Stability of Motion—Applications of Lyapunov's Second Method to Differential Systems and Equations with Delay*, Stanford University Press, Stanford, 1963.

[Kucera67] J. Kucera, "Solution in Large of Control Problem: $x=(Au+Bv)x$," from *Chech. Math. Journal*, vol. 17, pp. 91-96, 1967.

[Kurgan95] B. Kurganov, "Monocascade Enzyme Systems. Theoretical Analysis of Hysteretic Properties of the Enzyme Initiating the Cascade," from *Biochemistry*, vol. 60, no. 7, pp. 843-849, 1995.

[LarBoc09] Larhlimi, A., Bockmayr, A. (2009) A new constraint-based description of the steady-state flux cone of metabolic networks. Discrete Applied Mathematics. 157: 2257-2266.

[LaSLef61] J. La Salle and S. Lefschetz, from *Stability by Liapunov's Direct Method—With Applications (Mathematics in Science and Engineering*, Vol. 4, Academic Press, New York, 1961.

[Levine66] S. Levine, "Enzyme Amplifier Kinetics," from *Science*, v. 152, pp. 651-653, 1966.

[Ludwig80] L. F. Ludwig, *Bilinear Controllability Applied to a Geometric Variant of the Holding Problem*, M.S.E.E. thesis, Cornell University, Ithaca, 1980.

[LudwigTA] L. F. Ludwig, "Hysteretic Behaviors in Bilinear Systems," to appear.

[MacSch92] M. MacNicol, H. Schulman, "Crosstalk between Protein Kinase C and Multifunctional $Ca^{2+}$/Calmodulin-dependent Protein Kinase," The Journal of Biological Chemistry, vol. 267, No. 17, Jun. 15, 1992, pp. 12197-12201.

[Mendes01] Mendes, P. and Kell, D. B. (2001) MEG (Model Extender for Gepasi): A program for the modelling of complex, heterogeneous, cellular systems. Bioinformatics, 17(3), Mar. 17, 2001, 288-289.

[MesTak75] M. D. Mesarovic and Y. Takahara, *General Systems Theory: Mathematical Foundations*, Academic Press, New York, 1975.

[Murota87] K. Murota, *Systems Analysis by Graphs and Matroids—Structural Solvability and Controllability*, Springer-Verlag, New York, 1987.

[Mohler73] R. R. Mohler, Bilinear Control Processes (*Mathematics in Science and Engineering* v. 106), Academic Press, New York, 1973.

[Mohler79] R. R. Mohler, "Bilinear control structures in immunology," Lecture Notes in Control and Information Sciences, Springer, pp. 58-68, 1979.

[MusHin97] K. Musunuru and P. Hinds, *Cell Cycle Regulators in Cancer*, Karger Landes Systems, New York, 1997.

[PfScMS95] D. Pfeiffer, F. Scheller, C. McNeil and T. Schulmeister, "Cascade-like Exponential Substrate Amplification in Enzyme Sensors," from *Biosensors Bioelectronics*, pp. 169-180, Elsevier Advanced Technology, 1995.

[Potapo08] A. Potapov, "Signal Transduction and Gene Regulation Networks" in B. Junker, F. Schreiber, ed. Analysis of Biological Networks, John Wiley & Sons, Inc., Hoboken, 2008.

[PRPWP03] N. Price, J. Reed, J. Papin, S. Wiback, B. Palsson, "Network-based analysis of metabolic regulation in the human red blood cell," *Journal of Theoretical Biology*. 225, 2003, 185-194.

[PSPKSP04] J. Papin, J. Stelling, N. Price, S. Klamt, S. Schuster, B. Palsson, "Comparison of network-based pathway analysis methods," *Trends in Biotechnology*, 22(8), 2004, pp. 400-405.

[Roach77] P. J. Roach, "Functional Significance of Enzyme Cascade Systems," from *Trends in Biochemical Sciences*, vol. 2, no. 4, pp. 87-90, 1977.

[Robubi08] A. Robubi, *RAF Kinases: Pathway, Modulation and Modeling: New—Potentially Irreversible—Kinase Inhibitors, Computational Modeling of the Signaling Cascade, and the Effect of DiRas3 on RAF Signaling*, VDM Verlag Dr. Muller, 2008.

[RodRod64] N. M Rodiguin, E. N. Rodiguina, *Consecutive Chemical Reactions—Mathematical Analysis and Development*, (tr. R. F. Schneider), Van Nostrand Co., Inc., New York, 1964.

[Sander05] M. Sanderson, "Basic Concepts of Ca2+ Signaling in Cells and Tissues," in J. Sneyd, R. Bertram, J. Greenstein, R. Hinch, E. Pate, J. Reisert, M. Sanderson, T. Shannon, R. Wilson, *Tutorials in Mathematical Biosciences II: Mathematical Modeling of Calcium Dynamics and Signal Transduction* (Lecture Notes in Mathematics/Mathematical Biosciences Subseries) (v. 2), Springer, 2005.

[Shmitz98] A. Schmitz, *Investigations of Molecular Interactions of MARCKS-Related Protein: Cross-talk between Calmodulin and Protein Kinase C*, Department of Biochemistry, University of Basil, 1998.

[Shulma88] H. Schulman, "The Multifunctional Ca2+/Calmodulin-Dependent Protein Kinase," in Advances in Second Messenger and Phosphoprotein Research, Vol. 22, P. Greengard, G. Robison, ed., Raven Press, 1988.

[Schulze95] S. Schulze-Kremer, *Molecular Bioinformatics Algorithms and Applications*, Walter de Gruyer & Company, Berlin, 1995/1996, ISBN 3-11-014113-2

[SGMBE03] D. Soergel, B. George, R. Morgan-Linial, R. Brent, D. Endy, "Monod, A Tool to Support Collaborative Modeling of Biological Processes," available at): http://monod.molsci.org/docs/Monod-June-2003.pdf, Jun. 24, 2003.

[SKBSG02] J. Stelling, S. Klamt, K. Bettenbrock, S. Schuster, E. Gilles, "Metabolic network structure determines key aspects of functionality and regulation," *Nature* 420: pp. 190-193.

[StaCho78] E. R. Stadtman and P. B. Chock, "Interconvertible Enzyme Cascades in Metabolic Regulation," from *Current Topics in Cellular Regulation*, vol. 13, pp. 53-95, 1978.

[StElLe08] M. Stefan, S. Edelstein, N. Le Novere, "An Allosteric Model of Calmodulin explains Differential Activation of PP2B and CaMKII," PNAS, vol. 105, No. 31, Aug. 5, 2008, pp. 10768-10773.

[TeZeBo96] O. N. Temkin, A. V. Zeigarnik, D. Bonchev, *Chemical Reaction Networks—A Graph-Theoretical Approach*, CRC Press, New York, 1996.

[ThoTho78] J. S. Thorp and R. Thomas, *Theoretical Studies of Problems of Guaranteed Durability in Large Scale Electric Power Systems*, Research proposal submitted in response to PRDA ET-78-0-01-3088, 1978.

[Traut07] T. Traut, Regulatory Allosteric Enzymes, Springer, 2007.

[Walter73] C. Walter, "Stability Properties and Periodic Behavior of Controlled Biochemical Systems," from Nonlinear Problems in the *Physical Sciences and Biology* (*Lecture Notes in Mathematics*), pp. 343-357, Springer-Verlag, New York, 1973.

[Wiberg71] D. M. Wiberg, *State Space and Linear Systems*, McGraw-Hill Book Company, New York, 1971.

[VarHav90] R. Varon and B. H. Haysteen, "Kinetics of the Transient-Phase and Steady-State of the Monocyclic Enzyme Cascades," from *Journal Theor. Biol.*, vol. 144, pp. 397-413, 1990.

[Venter01] Venter, J. C., et al., "The Sequence of the Human Genome," *Science*, vol. 291, Feb. 16, 2001, pp. 1304-51.

[ZhaChe99] X-A. Zhang and L. Chen, "The Periodic Solution of a Class of Epidemic Models," from *Computers and Mathematics with Applications*, v. 38, pp. 61-71, Elsevier Science Ltd., 1999.

I claim:

1. A non-transitory computer readable medium comprising computer modeling software for use in the study of the dynamic behavior of biochemical signaling pathways, the computer modeling software having instructions configured for execution on a computer, comprising:
   a computer representation of a nonlinear model representing at least one biochemical signaling pathway, the computer representation comprising:
   a first set of computer instructions for transforming the computer representation into at least portions of a bilinear dynamical system representation comprising a multiplicative input, the portions comprising at least a linear transformation matrix and a multiplicative product term associated with the multiplicative input;
   a second set of computer instructions for using the portions to numerically compute a series of Lie bracket operations associated with the bilinear dynamical system representation, the computed series of Lie bracket operations resulting in a finite set of matrices; and
   a third set of computer instructions for using the Lie bracket operations to determine the controllability of the model with respect to variations in the multiplicative input, wherein the susceptibility of biochemical signaling pathway to selected disturbance effects is associated with the controllability of the model with respect to variations in the multiplicative input.

2. The non-transitory computer readable medium of claim 1 wherein the computer representation further comprises:
   at least two state variables, each state variable representing a physical quantity associated with at least one of the at least one signaling pathway;
   a multiplicative product between the at least two state variables; and
   a feedback loop.

3. The non-transitory computer readable medium of claim 1 wherein the susceptibility of the model to the instability from the variations in the multiplicative input is determined by a computer algorithm implementation of a Lie matrix algebra transitivity test.

4. The non-transitory computer readable medium of claim 1 wherein the computer modeling software provides at least one numerical simulation tool.

5. The non-transitory computer readable medium of claim 4 wherein the at least one numerical simulation tool is controlled by the computer representation of the nonlinear model.

6. The non-transitory computer readable medium of claim 1 wherein the computer modeling software provides at least one equilibrium condition tool.

7. The non-transitory computer readable medium of claim 6 wherein the at least one equilibrium condition tool is controlled by the computer representation of the nonlinear model.

8. The non-transitory computer readable medium of claim 1 wherein the computer modeling software provides at least one additional algebraic structure tool.

9. The non-transitory computer readable medium of claim 8 wherein the at least one additional algebraic structure tool is controlled by the computer representation of the nonlinear model.

10. The non-transitory computer readable medium of claim 8 wherein the at least one additional algebraic structure tool comprises a flux model.

11. The non-transitory computer readable medium of claim 8 wherein the at least one additional algebraic structure tool utilizes graph analysis.

12. The non-transitory computer readable medium of claim 8 wherein the at least one additional algebraic structure tool utilizes matroid analysis.

13. The non-transitory computer readable medium of claim 1 wherein the computer modeling software provides at least one crosstalk analysis tool.

14. The non-transitory computer readable medium of claim 1 wherein the computer modeling software additional provides at least one interactive user environment.

15. The non-transitory computer readable medium of claim 1 wherein the nonlinear model representing at least one biochemical signaling pathway comprises at least one enzyme cascade.

16. The non-transitory computer readable medium of claim 1 wherein the nonlinear model representing at least one biochemical signaling pathway comprises at least one allosteric enzyme.

17. The non-transitory computer readable medium of claim 1 wherein the nonlinear model representing at least one biochemical signaling pathway comprises at least one molecular switch.

18. The non-transitory computer readable medium of claim 1 wherein the nonlinear model representing at least one biochemical signaling pathway comprises at least one ion channel.

19. The non-transitory computer readable medium of claim 1 wherein the nonlinear model is in a modular format configured to be replaced with an alternate model subscribing to the same modular format.

20. The non-transitory computer readable medium of claim 1 wherein the computer modeling software accesses stored data over the internet.

* * * * *